(12) United States Patent
Eitan

(10) Patent No.: US 11,679,189 B2
(45) Date of Patent: Jun. 20, 2023

(54) FAST TEST FOR MEDICAL PUMP

(71) Applicant: EITAN MEDICAL LTD., Netanya (IL)

(72) Inventor: Boaz Eitan, Hofit (IL)

(73) Assignee: EITAN MEDICAL LTD., Netanya (IL)

( * ) Notice: Subject to any disclaimer, the term of this patent is extended or adjusted under 35 U.S.C. 154(b) by 353 days.

(21) Appl. No.: 16/950,149

(22) Filed: Nov. 17, 2020

(65) Prior Publication Data

US 2021/0146032 A1 May 20, 2021

Related U.S. Application Data

(60) Provisional application No. 62/936,941, filed on Nov. 18, 2019.

(51) Int. Cl.
*A61M 1/36* (2006.01)

(52) U.S. Cl.
CPC ........ *A61M 1/3626* (2013.01); *A61M 1/3629* (2014.02); *A61M 2205/3327* (2013.01)

(58) Field of Classification Search
None
See application file for complete search history.

(56) References Cited

U.S. PATENT DOCUMENTS

| | | | |
|---|---|---|---|
| 2,056,322 A | 10/1936 | Hoppe | |
| 2,393,838 A | 1/1946 | Tarbox | |
| 2,743,898 A | 5/1956 | King, Jr. | |
| 2,981,115 A | 4/1961 | Beguin | |
| 3,443,585 A | 5/1969 | Reinicke | |
| 3,511,583 A | 5/1970 | Brown | |
| 3,677,667 A | 7/1972 | Morrison | |
| 3,778,195 A | 12/1973 | Bamberg | |
| 3,982,722 A | 9/1976 | Bernard | |

(Continued)

FOREIGN PATENT DOCUMENTS

| | | |
|---|---|---|
| DE | 10118086 | 7/2002 |
| EP | 0215249 | 3/1987 |

(Continued)

OTHER PUBLICATIONS

An Office Action dated Sep. 30, 2019, which issued during the prosecution of U.S. Appl. No. 15/740,365.

(Continued)

*Primary Examiner* — Krishnan S Menon
(74) *Attorney, Agent, or Firm* — The Roy Gross Law Firm, LLC; Roy Gross

(57) ABSTRACT

A method and apparatus are provided for use with a pump. The method includes, (a) placing liquid in a tube coupled to the pump, (b) injecting an air bubble into the tube in a manner that does not increase pressure within the tube, and such that there is a predetermined volume of liquid between the air bubble and the pump, (c) using the pump to advance the air bubble along the tube to the bubble detector of the pump, (d) using the pump, assessing accuracy of the pump by automatically measuring the volume of liquid pumped to advance the air bubble to the bubble detector, and (e) using the pump to continue advancing the air bubble along the tube, past the bubble detector, and using the pump to measure a volume of the air bubble. Other applications are also described.

18 Claims, 25 Drawing Sheets

(56) References Cited

U.S. PATENT DOCUMENTS

| | | |
|---|---|---|
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,178,138 A | 12/1979 | Iles |
| 4,236,880 A | 12/1980 | Archibald |
| 4,270,532 A | 6/1981 | Franetzki et al. |
| 4,290,346 A | 9/1981 | Bujan |
| 4,320,781 A | 3/1982 | Bouvet et al. |
| 4,373,525 A | 2/1983 | Kobayashi |
| 4,450,375 A | 5/1984 | Siegal |
| 4,479,797 A | 10/1984 | Kobayashi et al. |
| 4,489,863 A | 12/1984 | Horchos et al. |
| 4,493,706 A | 1/1985 | Borsanyi et al. |
| 4,650,469 A | 3/1987 | Berg et al. |
| 4,671,792 A | 6/1987 | Borsanyi |
| 4,682,135 A | 7/1987 | Yamakawa |
| 4,690,673 A | 9/1987 | Bloomquist |
| 4,725,205 A | 2/1988 | Cannon et al. |
| 4,725,407 A * | 2/1988 | Usui ............... G01N 35/08 422/82 |
| 4,728,265 A | 3/1988 | Cannon |
| 4,741,736 A | 5/1988 | Brown |
| 4,748,003 A | 5/1988 | Riley |
| 4,755,168 A | 7/1988 | Romanelli et al. |
| 4,836,752 A | 6/1989 | Burkett |
| 4,867,744 A | 9/1989 | Borsanyi |
| 4,893,991 A | 1/1990 | Heminway et al. |
| 4,927,411 A | 5/1990 | Pastrone et al. |
| 4,954,046 A | 9/1990 | Irvin et al. |
| 4,954,256 A | 9/1990 | Degen et al. |
| 4,978,335 A | 12/1990 | Arthur, III |
| 4,981,467 A * | 1/1991 | Bobo, Jr. ............... A61M 5/365 604/122 |
| 5,074,756 A | 12/1991 | Davis |
| 5,078,683 A | 1/1992 | Sancoff et al. |
| 5,088,904 A | 2/1992 | Okada |
| 5,096,385 A | 3/1992 | Georgi et al. |
| 5,103,211 A | 4/1992 | Daoud et al. |
| 5,151,019 A | 9/1992 | Danby et al. |
| 5,152,680 A | 10/1992 | Okada |
| 5,165,874 A | 11/1992 | Sancoff et al. |
| 5,213,483 A | 5/1993 | Flaherty et al. |
| 5,219,327 A | 6/1993 | Okada |
| 5,222,946 A | 6/1993 | Kamen |
| 5,246,347 A | 9/1993 | Davis |
| 5,257,978 A | 11/1993 | Haber et al. |
| 5,286,176 A | 2/1994 | Bonin |
| 5,290,158 A | 3/1994 | Okada |
| 5,308,333 A | 5/1994 | Skakoon |
| 5,338,157 A | 8/1994 | Blomquist |
| 5,395,320 A | 3/1995 | Padda et al. |
| 5,429,485 A | 7/1995 | Dodge |
| 5,485,408 A | 1/1996 | Blomquist |
| 5,499,969 A | 3/1996 | Beuchat et al. |
| 5,509,439 A | 4/1996 | Tantardini |
| 5,527,295 A | 6/1996 | Wing |
| 5,542,826 A | 8/1996 | Warner |
| 5,569,188 A | 10/1996 | Mackool |
| 5,575,309 A | 11/1996 | Connell |
| 5,575,631 A | 11/1996 | Jester |
| 5,577,891 A | 11/1996 | Loughnane et al. |
| 5,584,667 A | 12/1996 | Davis |
| 5,593,134 A | 1/1997 | Steber et al. |
| 5,601,420 A | 2/1997 | Warner et al. |
| 5,628,619 A | 5/1997 | Wilson |
| 5,658,250 A | 8/1997 | Blomquist et al. |
| 5,658,252 A | 8/1997 | Johnson |
| 5,660,529 A | 8/1997 | Hill |
| 5,669,877 A | 9/1997 | Blomquist |
| 5,683,233 A | 11/1997 | Moubayed et al. |
| 5,695,473 A | 12/1997 | Olsen |
| 5,704,584 A | 1/1998 | Winterer et al. |
| 5,742,519 A | 4/1998 | McClendon et al. |
| 5,782,805 A | 7/1998 | Meinzer et al. |
| 5,788,669 A | 8/1998 | Peterson |
| 5,791,880 A | 8/1998 | Wilson |
| 5,791,881 A | 8/1998 | Moubayed et al. |
| 5,803,712 A | 9/1998 | Davis et al. |
| 5,807,322 A | 9/1998 | Lindsey et al. |
| 5,810,323 A | 9/1998 | Winterer et al. |
| 5,843,035 A | 12/1998 | Bowman et al. |
| 5,853,386 A | 12/1998 | Davis et al. |
| 5,876,370 A | 3/1999 | Blomquist |
| 5,888,052 A | 3/1999 | Hill |
| 5,896,076 A | 4/1999 | Van Namen |
| 5,909,724 A | 6/1999 | Nishimura et al. |
| 5,924,852 A | 7/1999 | Moubayed et al. |
| 5,935,099 A | 8/1999 | Peterson et al. |
| 5,935,106 A | 8/1999 | Olsen |
| 5,943,633 A | 8/1999 | Wilson et al. |
| 5,954,485 A | 9/1999 | Johnson et al. |
| 5,980,490 A | 11/1999 | Tsoukalis |
| 5,996,964 A | 12/1999 | Ben-Shalom |
| 6,024,539 A | 2/2000 | Blomquist |
| 6,095,189 A | 8/2000 | Ben-Shalom |
| 6,110,153 A | 8/2000 | Davis et al. |
| 6,146,109 A | 11/2000 | Davis et al. |
| 6,164,921 A | 12/2000 | Moubayed et al. |
| 6,165,874 A | 12/2000 | Powell et al. |
| RE37,074 E | 2/2001 | Danby et al. |
| 6,203,296 B1 | 3/2001 | Ray et al. |
| 6,213,723 B1 | 4/2001 | Danby et al. |
| 6,213,739 B1 | 4/2001 | Phallen et al. |
| 6,234,773 B1 | 5/2001 | Hill et al. |
| 6,241,704 B1 | 6/2001 | Peterson et al. |
| 6,261,262 B1 | 7/2001 | Briggs et al. |
| 6,280,408 B1 | 8/2001 | Sipin |
| 6,312,227 B1 | 11/2001 | Davis |
| 6,339,410 B1 | 1/2002 | Milner et al. |
| 6,347,553 B1 | 2/2002 | Morris et al. |
| 6,371,732 B1 | 4/2002 | Moubayed et al. |
| 6,422,057 B1 | 7/2002 | Anderson |
| 6,450,773 B1 | 9/2002 | Upton |
| 6,475,180 B2 | 11/2002 | Peterson et al. |
| 6,519,569 B1 | 2/2003 | White et al. |
| 6,537,244 B2 | 3/2003 | Paukovits et al. |
| 6,544,171 B2 | 4/2003 | Beetz et al. |
| 6,558,347 B1 | 5/2003 | Jhuboo et al. |
| 6,572,604 B1 | 6/2003 | Platt et al. |
| 6,622,542 B2 | 9/2003 | Derek et al. |
| 6,648,861 B2 | 11/2003 | Platt et al. |
| 6,692,241 B2 | 2/2004 | Watanabe et al. |
| 6,733,476 B2 | 5/2004 | Christenson et al. |
| 6,742,992 B2 | 6/2004 | Davis |
| 6,749,587 B2 | 6/2004 | Flaherty |
| 6,768,425 B2 | 7/2004 | Flaherty et al. |
| 6,788,199 B2 | 9/2004 | Crabtree et al. |
| 6,790,198 B1 | 9/2004 | White et al. |
| 6,902,549 B2 | 6/2005 | Marmaropoulos et al. |
| 6,942,473 B2 | 9/2005 | Abrahamson et al. |
| 7,018,361 B2 | 3/2006 | Gillespie, Jr. et al. |
| 7,022,075 B2 | 4/2006 | Grunwald et al. |
| 7,048,720 B1 | 5/2006 | Thorne, Jr. et al. |
| 7,059,840 B2 | 6/2006 | Corwin et al. |
| 7,122,026 B2 | 10/2006 | Rogers et al. |
| 7,131,966 B1 | 11/2006 | Tamari |
| 7,163,385 B2 | 1/2007 | Gharib et al. |
| 7,347,836 B2 | 3/2008 | Peterson et al. |
| 7,525,432 B2 | 4/2009 | Jackson |
| 7,556,481 B2 | 7/2009 | Moubayed |
| 7,645,258 B2 | 1/2010 | White et al. |
| 7,654,976 B2 | 2/2010 | Peterson et al. |
| 7,695,255 B2 | 4/2010 | Ben-shalom et al. |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |

(56) References Cited

U.S. PATENT DOCUMENTS

| | | |
|---|---|---|
| 8,025,634 B1 | 9/2011 | Moubayed et al. |
| 8,029,253 B2 | 10/2011 | Rotem et al. |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 9,194,390 B1 * | 11/2015 | Ruiter .................... F04B 53/10 |
| 9,726,167 B2 | 8/2017 | Schweitzer et al. |
| 10,894,131 B2 | 1/2021 | Eitan et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 | 11/2002 | Morris et al. |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141468 A1 | 7/2003 | Malmstrom et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0107923 A1 | 5/2005 | Vanderveen |
| 2005/0112001 A1 | 5/2005 | Bahnen et al. |
| 2005/0171501 A1 | 8/2005 | Kelly |
| 2005/0191196 A1 | 9/2005 | Tanner et al. |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173412 A1 | 8/2006 | Susi |
| 2006/0173419 A1 | 8/2006 | Malcolm |
| 2006/0189926 A1 | 8/2006 | Hall et al. |
| 2006/0213249 A1 | 9/2006 | Uram et al. |
| 2007/0032098 A1 | 2/2007 | Bowles et al. |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0123781 A1 | 5/2007 | Callahan et al. |
| 2007/0135866 A1 | 6/2007 | Baker et al. |
| 2007/0154336 A1 | 7/2007 | Miyazaki et al. |
| 2007/0179435 A1 | 8/2007 | Braig et al. |
| 2007/0217931 A1 | 9/2007 | Estes et al. |
| 2007/0269324 A1 | 11/2007 | Goldor et al. |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 | 4/2008 | Ben-Shalom et al. |
| 2008/0144560 A1 | 6/2008 | Jia et al. |
| 2008/0145249 A1 | 6/2008 | Smisson et al. |
| 2008/0146995 A1 | 6/2008 | Smisson et al. |
| 2008/0275307 A1 | 11/2008 | Poschmann |
| 2008/0283296 A1 | 11/2008 | Zamora et al. |
| 2009/0031797 A1 * | 2/2009 | Das .................... G01F 1/007 73/227 |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1 | 9/2009 | Rotem et al. |
| 2009/0240201 A1 | 9/2009 | Rotem et al. |
| 2009/0270810 A1 | 10/2009 | Debelser et al. |
| 2009/0293588 A1 | 12/2009 | Riley et al. |
| 2009/0300507 A1 | 12/2009 | Raghavan et al. |
| 2009/0317268 A1 | 12/2009 | Rotem et al. |
| 2010/0016781 A1 | 1/2010 | Nakayama et al. |
| 2010/0036322 A1 | 2/2010 | Rotem |
| 2010/0082001 A1 | 4/2010 | Beck et al. |
| 2010/0168545 A1 | 7/2010 | Kamath et al. |
| 2010/0211002 A1 | 8/2010 | Davis |
| 2010/0212407 A1 | 8/2010 | Stringham et al. |
| 2010/0218586 A1 | 9/2010 | Rosinko et al. |
| 2010/0228223 A1 | 9/2010 | Williams et al. |
| 2010/0234708 A1 | 9/2010 | Buck et al. |
| 2010/0279652 A1 | 11/2010 | Sharp et al. |
| 2011/0148624 A1 | 6/2011 | Eaton et al. |
| 2011/0152772 A1 | 6/2011 | Rotem et al. |
| 2011/0152831 A1 | 6/2011 | Rotem et al. |
| 2011/0167133 A1 | 7/2011 | Jain |
| 2011/0190606 A1 | 8/2011 | Gable et al. |
| 2011/0251856 A1 | 10/2011 | Maus et al. |
| 2011/0264043 A1 | 10/2011 | Kotnik et al. |
| 2011/0276000 A1 | 11/2011 | Stringham |
| 2011/0282291 A1 | 11/2011 | Ciccone |
| 2011/0318208 A1 | 12/2011 | Goldor et al. |
| 2012/0059389 A1 | 3/2012 | Larson et al. |
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2012/0330574 A1 | 12/2012 | Ruiter et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0226129 A1 | 8/2013 | Unverdorben |
| 2013/0279370 A1 | 10/2013 | Eitan et al. |
| 2013/0345623 A1 | 12/2013 | Kopperschmidt et al. |
| 2014/0005631 A1 | 1/2014 | Rotem et al. |
| 2014/0048460 A1 | 2/2014 | Paolini et al. |
| 2014/0119954 A1 | 5/2014 | Schweitzer et al. |
| 2014/0121639 A1 | 5/2014 | Lowery et al. |
| 2014/0197824 A1 | 7/2014 | Gillespie et al. |
| 2014/0222377 A1 | 8/2014 | Bitan et al. |
| 2014/0228755 A1 | 8/2014 | Darrah et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0005699 A1 | 1/2015 | Burbank et al. |
| 2015/0038187 A1 | 2/2015 | Ho et al. |
| 2015/0073338 A1 | 3/2015 | Waldhoff et al. |
| 2015/0105726 A1 | 4/2015 | Qi et al. |
| 2015/0122052 A1 | 5/2015 | Rosinko et al. |
| 2015/0137988 A1 | 5/2015 | Gravenstein et al. |
| 2015/0141955 A1 | 5/2015 | Ruchti et al. |
| 2015/0172921 A1 | 6/2015 | Wang et al. |
| 2015/0182694 A1 | 7/2015 | Rosinko |
| 2015/0192120 A1 | 7/2015 | Rotem et al. |

(56) References Cited

U.S. PATENT DOCUMENTS

| | | |
|---|---|---|
| 2015/0367120 A1 | 12/2015 | Kusters |
| 2018/0200456 A1 | 7/2018 | Eitan et al. |

FOREIGN PATENT DOCUMENTS

| | | |
|---|---|---|
| EP | 0225158 | 6/1987 |
| EP | 0315312 | 5/1989 |
| EP | 0429866 | 6/1991 |
| EP | 0483794 | 5/1992 |
| EP | 0858812 | 8/1998 |
| EP | 1031358 | 8/2000 |
| EP | 1350955 | 10/2003 |
| EP | 1557186 | 7/2005 |
| EP | 1611834 | 1/2006 |
| EP | 1485149 | 7/2008 |
| FR | 2632529 | 12/1989 |
| FR | 2753236 | 3/1998 |
| JP | S60-43188 | 3/1985 |
| JP | H06-169992 | 6/1994 |
| JP | 2002-057738 | 2/2002 |
| JP | 2004141418 | 5/2004 |
| WO | 8400691 | 3/1984 |
| WO | 9116933 | 11/1991 |
| WO | 9325816 | 12/1993 |
| WO | 9408647 | 4/1994 |
| WO | 9603168 | 2/1996 |
| WO | 9630679 | 10/1996 |
| WO | 9734084 | 9/1997 |
| WO | 9804301 | 2/1998 |
| WO | 9813080 | 4/1998 |
| WO | 9847551 | 10/1998 |
| WO | 9958178 | 11/1999 |
| WO | 0139816 | 6/2001 |
| WO | 0165232 | 9/2001 |
| WO | 0236044 | 5/2002 |
| WO | 0238204 | 5/2002 |
| WO | 0249509 | 6/2002 |
| WO | 02068015 | 9/2002 |
| WO | 03027503 | 4/2003 |
| WO | 03080158 | 10/2003 |
| WO | 2004/070548 | 8/2004 |
| WO | 2004/093648 | 11/2004 |
| WO | 2005/089263 | 9/2005 |
| WO | 2006/056986 | 6/2006 |
| WO | 2007/133259 | 11/2007 |
| WO | 2008/036658 | 3/2008 |
| WO | 2008/059492 | 5/2008 |
| WO | 2008/059493 | 5/2008 |
| WO | 2008/059495 | 5/2008 |
| WO | 2008/059496 | 5/2008 |
| WO | 2008/059498 | 5/2008 |
| WO | 2008/059499 | 5/2008 |
| WO | 2008059494 | 5/2008 |
| WO | 2008/130644 | 10/2008 |
| WO | 2009/042061 | 4/2009 |
| WO | 2009/047721 | 4/2009 |
| WO | 2010/053702 | 5/2010 |
| WO | 2010/053703 | 5/2010 |
| WO | 2010/091313 | 8/2010 |
| WO | 2011/128850 | 10/2011 |
| WO | 2012/095827 | 7/2012 |
| WO | 2012/095829 | 7/2012 |
| WO | 2013/001425 | 1/2013 |
| WO | 2013/028704 | 2/2013 |
| WO | 2013/090748 | 6/2013 |
| WO | 2017/002023 | 1/2017 |
| WO | 20170184777 A1 | 10/2017 |

OTHER PUBLICATIONS

An Office Action together with an English summary dated Jun. 23, 2020, which issued during the prosecution of Chinese Patent Application No. 201690050050.8.

An International Search Report and a Written Opinion both dated May 30, 2012, which issued during the prosecution of Applicant's PCT/IB2012/050189.

An International Preliminary Report on Patentability dated May 19, 2009, which issued during the prosecution of Applicant's PCT/IL2007/001405.

An International Preliminary Report on Patentability dated May 19, 2009, which issued during the prosecution of Applicant's PCT/IL2007/001404.

An International Preliminary Report on Patentability dated May 19, 2009, which issued during the prosecution of Applicant's PCT/IL2007/001402.

An International Preliminary Report on Patentability dated May 19, 2009, which issued during the prosecution of Applicant's PCT/IL2007/001401.

An International Preliminary Report on Patentability dated May 19, 2009, which issued during the prosecution of Applicant's PCT/IL2007/001400.

An International Preliminary Report on Patentability dated May 19, 2009, which issued during the prosecution of Applicant's PCT/IL2007/001399.

An International Preliminary Report on Patentability dated May 19, 2009, which issued during the prosecution of Applicant's PCT/IL2007/001398.

An International Search Report and a Written Opinion both dated Jun. 25, 2015, which issued during the prosecution of Applicant's PCT/IB2015/050873.

An International Search Report and a Written Opinion both dated Feb. 24, 2015, which issued during the prosecution of Applicant's PCT/IB2014/062106.

European Search Report dated Jun. 21, 2019 which issued during the prosecution of Applicant's European App No. 16817348.2.

An International Preliminary Report on Patentability dated Oct. 16, 2012, which issued during the prosecution of Applicant's PCT/IB2011/051586.

An International Preliminary Report on Patentability dated Jul. 16, 2013, which issued during the prosecution of Applicant's PCT/IB2012/050189.

An International Preliminary Report on Patentability dated Jul. 16, 2013, which issued during the prosecution of Applicant's PCT/IB2012/050192.

An Office Action dated Feb. 2, 2009, which issued during the prosecution of U.S. Appl. No. 10/535,103.

An Office Action dated Aug. 19, 2010, which issued during the prosecution of U.S. Appl. No. 11/791,599.

An Office Action dated Mar. 31, 2011, which issued during the prosecution of U.S. Appl. No. 11/791,599.

Notice of Allowance dated Sep. 21, 2020, which issued during the prosecution of U.S. Appl. No. 15/740,365.

An Office Action dated Jun. 22, 2020, which issued during the prosecution of U.S. Appl. No. 15/740,365.

An Office Action dated Dec. 13, 2011, which issued during the prosecution of U.S. Appl. No. 12/463,399.

An Office Action dated Jul. 21, 2011, which issued during the prosecution of U.S. Appl. No. 12/463,399.

An Office Action dated Jan. 20, 2012, which issued during the prosecution of U.S. Appl. No. 12/514,310.

An Office Action dated Jul. 21, 2011, which issued during the prosecution of U.S. Appl. No. 12/514,310.

An Office Action dated May 25, 2012, which issued during the prosecution of U.S. Appl. No. 12/514,310.

U.S. Appl. No. 62/278,617, filed Jan. 14, 2016.

U.S. Appl. No. 62/185,737, filed Jun. 29, 2015.

An Office Action dated Apr. 20, 2015, which issued during the prosecution of U.S. Appl. No. 12/514,311.

An Office Action dated Feb. 18, 2011, which issued during the prosecution of U.S. Appl. No. 12/514,311.

An Office Action dated Oct. 7, 2014, which issued during the prosecution of U.S. Appl. No. 12/514,311.

An Office Action dated Sep. 16, 2010, which issued during the prosecution of U.S. Appl. No. 12/514,311.

An Office Action dated Apr. 6, 2012, which issued during the prosecution of U.S. Appl. No. 12/644,026.

(56) References Cited

OTHER PUBLICATIONS

An Office Action dated Apr. 28, 2011, which issued during the prosecution of U.S. Appl. No. 12/644,027.
An Office Action dated Aug. 19, 2014, which issued during the prosecution of U.S. Appl. No. 13/651,420.
U.S. Appl. No. 62/936,941, filed Nov. 18, 2019.
An Office Action dated Apr. 24, 2014, which issued during the prosecution of U.S. Appl. No. 13/651,420.
An Office Action dated Jan. 6, 2014, which issued during the prosecution of U.S. Appl. No. 13/651,420.
An Office Action dated Jun. 9, 2015, which issued during the prosecution of U.S. Appl. No. 13/651,420.
An Office Action dated Mar. 16, 2015, which issued during the prosecution of U.S. Appl. No. 13/651,420.
An Office Action dated Nov. 4, 2013, which issued during the prosecution of U.S. Appl. No. 13/651,420.
An Office Action dated Apr. 24, 2015, which issued during the prosecution of U.S. Appl. No. 13/681,440.
An Office Action dated Feb. 14, 2014, which issued during the prosecution of U.S. Appl. No. 13/681,440.
An Office Action dated Oct. 24, 2013, which issued during the prosecution of U.S. Appl. No. 13/681,440.
An Office Action dated Sep. 2, 2014, which issued during the prosecution of U.S. Appl. No. 13/681,440.
An Office Action dated Mar. 28, 2014, which issued during the prosecution of U.S. Appl. No. 13/742,454.
An Office Action dated Oct. 7, 2013, which issued during the prosecution of U.S. Appl. No. 13/742,454.
An Office Action dated Dec. 2, 2014, which issued during the prosecution of U.S. Appl. No. 13/924,572.
An Office Action dated May 14, 2015, which issued during the prosecution of U.S. Appl. No. 13/924,572.
An Office Action dated Jan. 23, 2015, which issued during the prosecution of U.S. Appl. No. 13/978,538.
An Office Action dated Jul. 24, 2015, which issued during the prosecution of U.S. Appl. No. 13/978,538.
An Office Action dated Oct. 15, 2014, which issued during the prosecution of U.S. Appl. No. 14/016,105.
An Office Action dated Jun. 3, 2015, which issued during the prosecution of U.S. Appl. No. 14/181,673.
An Office Action dated Dec. 24, 2013, which issued during the prosecution of U.S. Appl. No. 13/640,519.
An Office Action dated Mar. 20, 2014, which issued during the prosecution of U.S. Appl. No. 13/640,519.
An Office Action dated May 6, 2015, which issued during the prosecution of U.S. Appl. No. 13/640,519.
An Office Action dated Oct. 1, 2014, which issued during the prosecution of U.S. Appl. No. 13/640,519.
An Office Action dated Jun. 21, 2013, which issued during the prosecution of U.S. Appl. No. 13/229,798.
An Office Action dated Dec. 26, 2012, which issued during the prosecution of U.S. Appl. No. 13/229,798.
An Office Action dated Oct. 3, 2011, which issued during the prosecution of U.S. Appl. No. 12/464,202.
An Office Action dated Jul. 5, 1999, which issued during the prosecution of U.S. Appl. No. 09/125,438.
An Office Action dated May 3, 1999, which issued during the prosecution of U.S. Appl. No. 09/125,438.
An Advisory Action dated Jul. 1, 2015, which issued during the prosecution of U.S. Appl. No. 12/514,311.
An Advisory Action dated Aug. 5, 2015, which issued during the prosecution of U.S. Appl. No. 12/514,311.
An Advisory Action dated Mar. 8, 2012, which issued during the prosecution of U.S. Appl. No. 12/463,399.
An Office Action dated Jan. 23, 2012, which issued during the prosecution of European Patent Application No. 05810500.8.
An Office Action dated Jul. 6, 2009, which issued during the prosecution of European Patent Application No. 05810500.8.
An Office Action dated Nov. 3, 2014, which issued during the prosecution of European Patent Application No. 05810500.8.
An Office Action dated Jul. 6, 2015, which issued during the prosecution of European Patent Application No. 10192477.7.
An Office Action together with an English translation dated Jul. 13, 2010, which issued during the prosecution of Chinese Patent Application No. 200780041966.8.
An Office Action together with an English translation dated Jul. 18, 2008, which issued during the prosecution of Chinese Patent Application No. 200580045471.3.
An English translation of Notice of Allowance dated Jan. 28, 2011, which issued during the prosecution of Chinese Patent Application No. 200780041966.8.
An International Search Report dated Oct. 27, 2011, which issued during the prosecution of Applicant's PCT/IB2011/051586.
An International Search Report dated Aug. 17, 2012, which issued during the prosecution of Applicant's PCT/IB2012/050192.
An International Search Report dated Jan. 15, 2013, which issued during the prosecution of Applicant's PCT/IB2012/053149.
An International Search Report dated Jun. 11, 2008, which issued during the prosecution of Applicant's PCT/IL2007/001398.
An International Search Report dated Jan. 27, 1998, which issued during the prosecution of Applicant's PCT/IL1997/000289.
An International Search Report dated Jan. 27, 1998, which issued during the prosecution of Applicant's PCT/IL1997/000290.
An International Search Report dated Mar. 3, 2004, which issued during the prosecution of Applicant's PCT/IL2003/000947.
An International Search Report dated Apr. 5, 2006, which issued during the prosecution of Applicant's PCT/IL2005/001249.
An International Search Report dated Jun. 4, 2008, which issued during the prosecution of Applicant's PCT/IL2007/001399.
An International Search Report dated Jul. 15, 2008, which issued during the prosecution of Applicant's PCT/IL2007/001400.
An International Search Report dated Sep. 24, 2008, which issued during the prosecution of Applicant's PCT/IL2007/001401.
An International Search Report dated Jun. 20, 2008, which issued during the prosecution of Applicant s PCT/IL2007/001402.
An International Search Report dated Jul. 14, 2008, which issued during the prosecution of Applicant's PCT/IL2007/001404.
An International Search Report dated Jul. 21, 2008, which issued during the prosecution of Applicant's PCT/IL2007/001405.
Notice of Allowance dated Jun. 14, 2011, which issued during the prosecution of U.S. Appl. No. 11/791,599.
Notice of Allowance dated Apr. 29, 2013, which issued during the prosecution of U.S. Appl. No. 12/463,399.
Notice of Allowance dated Jul. 11, 2012, which issued during the prosecution of U.S. Appl. No. 12/464,202.
Notice of Allowance dated Aug. 22, 2012, which issued during the prosecution of U.S. Appl. No. 12/514,310.
Notice of Allowance dated Oct. 11, 2012, which issued during the prosecution of U.S. Appl. No. 12/644,026.
Notice of Allowance dated Nov. 17, 2011, which issued during the prosecution of U.S. Appl. No. 12/644,027.
Notice of Allowance dated Apr. 19, 2013, which issued during the prosecution of U.S. Appl. No. 13/229,798.
Notice of Allowance dated Nov. 14, 2013, which issued during the prosecution of U.S. Appl. No. 13/229,798.
Notice of Allowance dated Aug. 21, 2014, which issued during the prosecution of U.S. Appl. No. 13/742,454.
Notice of Allowance dated Feb. 17, 2015, which issued during the prosecution of U.S. Appl. No. 14/016,105.
Notice of Withdrawal from Issue dated May 13, 2013, which issued during the prosecution of U.S. Appl. No. 13/229,798.
An Interview Summary dated Mar. 4, 2011, which issued during the prosecution of U.S. Appl. No. 12/514,311.
An Office Action dated Dec. 31, 2014, which issued during the prosecution of Indian Patent Application No. 2344KOLNP2007.
European Search Report dated May 10, 2011 which issued during the prosecution of Applicant's European App No. 10192477.7.
European Search Report dated Aug. 18, 2014 which issued during the prosecution of Applicant's European App No. 12734200.4.
Partial European Search Report dated Feb. 23, 2015 which issued during the prosecution of Applicant's European App No. 12805094.5.

(56) References Cited

OTHER PUBLICATIONS

Partial European Search Report dated Nov. 13, 2014 which issued during the prosecution of Applicant's European App No. 11768544.6.
A Response dated Dec. 28, 2011to a European Search Report which issued during the prosecution of Applicant's European App No. 10192477.7.
A Response dated Apr. 2, 2015 to a European Search Report which issued during the prosecution of Applicant's European App No. 12805094.5.
European Search Report dated Jun. 30, 2015 which issued during the prosecution of Applicant's European App No. 12805094.5.
A Response to an Office Action which issued during the prosecution of U.S. Appl. No. 11/791,599 dated Jan. 11, 2011.
A Response to an Office Action which issued during the prosecution of U.S. Appl. No. 11/791,599 dated May 23, 2011.
A Response to an Office Action which issued during the prosecution of U.S. Appl. No. 12/463,399 dated Feb. 12, 2012.
A Response to an Office Action which issued during the prosecution of U.S. Appl. No. 12/463,399 dated Oct. 21, 2011.
A Response to an Office Action which issued during the prosecution of U.S. Appl. No. 12/464,202 dated Feb. 12, 2012.
A Response to an Office Action which issued during the prosecution of U.S. Appl. No. 12/514,310 dated Jun. 28, 2012.
A Response to an Office Action which issued during the prosecution of U.S. Appl. No. 12/514,310 dated Oct. 21, 2011.
A Response to an Office Action which issued during the prosecution of U.S. Appl. No. 12/514,311 dated Dec. 9, 2010.
A Response to an Office Action which issued during the prosecution of U.S. Appl. No. 12/514,311 dated Jan. 7, 2015.
A Response to an Office Action which issued during the prosecution of U.S. Appl. No. 12/514,311 dated Jun. 21, 2015.
A Response to an Office Action which issued during the prosecution of U.S. Appl. No. 12/644,026 dated Jul. 5, 2012.
A Response to an Office Action which issued during the prosecution of U.S. Appl. No. 12/644,027 dated Jul. 21, 2012.
A Response to an Office Action which issued during the prosecution of U.S. Appl. No. 13/299,798 dated Mar. 21, 2013.
A Response to an Office Action which issued during the prosecution of U.S. Appl. No. 13/299,798 dated Oct. 21, 2013.
Request for Continued Examination and a Response to an Office Action which issued during the prosecution of U.S. Appl. No. 12/463,399 dated Mar. 26, 2012.
Request for Continued Examination and a Response to an Office Action which issued during the prosecution of U.S. Appl. No. 12/514,310 dated Apr. 25, 2012.
Request for Continued Examination and a Response to an Office Action which issued during the prosecution of U.S. Appl. No. 12/514,311 dated Mar. 31, 2011.
Request for Continued Examination and a Response to an Office Action which issued during the prosecution of U.S. Appl. No. 13/651,420 dated Jul. 22, 2014.
Request for Continued Examination and a Response to an Office Action which issued during the prosecution of U.S. Appl. No. 13/681,440 dated Jul. 14, 2014.
Request for Continued Examination and a Response to an Office Action which issued during the prosecution of U.S. Appl. No. 13/742,454 dated Jun. 29, 2014.
Honeywell Sensing and Control, "FSSI500NSB force sensor", Golden Valley, Minnesota, USA, 1998-2004 http://sccatalog.honeywell.com/imc/printfriendly.asp7FAM~force&PN-FSSI500NSB (5 pages).
A Response to an Office Action which issued during the prosecution of U.S. Appl. No. 14/016,105 dated Jan. 14, 2015.
A Response to an Office Action which issued during the prosecution of U.S. Appl. No. 13/978,538 dated May 21, 2015.
A Response to an Office Action which issued during the prosecution of U.S. Appl. No. 13/924,572 dated Mar. 26, 2015.
A Response to an Office Action which issued during the prosecution of U.S. Appl. No. 13/742,454 dated Jan. 6, 2014.
A Response to an Office Action which issued during the prosecution of U.S. Appl. No. 13/681,440 dated Jan. 20, 2014.
A Response to an Office Action which issued during the prosecution of U.S. Appl. No. 13/651,420 dated Nov. 21, 2013.
A Response to an Office Action which issued during the prosecution of U.S. Appl. No. 13/651,420 dated May 14, 2015.
A Response to an Office Action which issued during the prosecution of U.S. Appl. No. 13/651,420 dated Mar. 5, 2014.
A Response to an Office Action which issued during the prosecution of U.S. Appl. No. 13/651,420 dated Dec. 18, 2014.
A Response to an Office Action which issued during the prosecution of U.S. Appl. No. 13/640,519 dated Jun. 17, 2014.
A Response to an Office Action which issued during the prosecution of U.S. Appl. No. 13/640,519 dated Jan. 16, 2014.
A Response to an Office Action which issued during the prosecution of U.S. Appl. No. 13/640,519 dated Dec. 28, 2014.
A Response to an Advisory Action which issued during the prosecution of U.S. Appl. No. 12/514,311 dated Jul. 20, 2015.
A Response to an Office Action which issued during the prosecution of European Patent Application No. 05810500.8 dated May 22, 2012.
A Response to an Office Action which issued during the prosecution of European Patent Application No. 05810500.8 dated Oct. 15, 2009.
A Response to an Office Action which issued during the prosecution of European Patent Application No. 05810500.8 dated Mar. 9, 2015.
A Response to an Office Action which issued during the prosecution of European Patent Application No. 13734200.4 dated Mar. 4, 2015.
A Response to an Office Action which issued during the prosecution of European Patent Application No. 11768544.6 dated May 29, 2015.
A Response to an Office Action which issued during the prosecution of Indian Patent Application No. 2344KOLNP2007 dated Aug. 7, 2015.
European Search Repod dated Apr. 22, 2021 which issued during the prosecution of Applicant's European App No. 20208122.0.

* cited by examiner

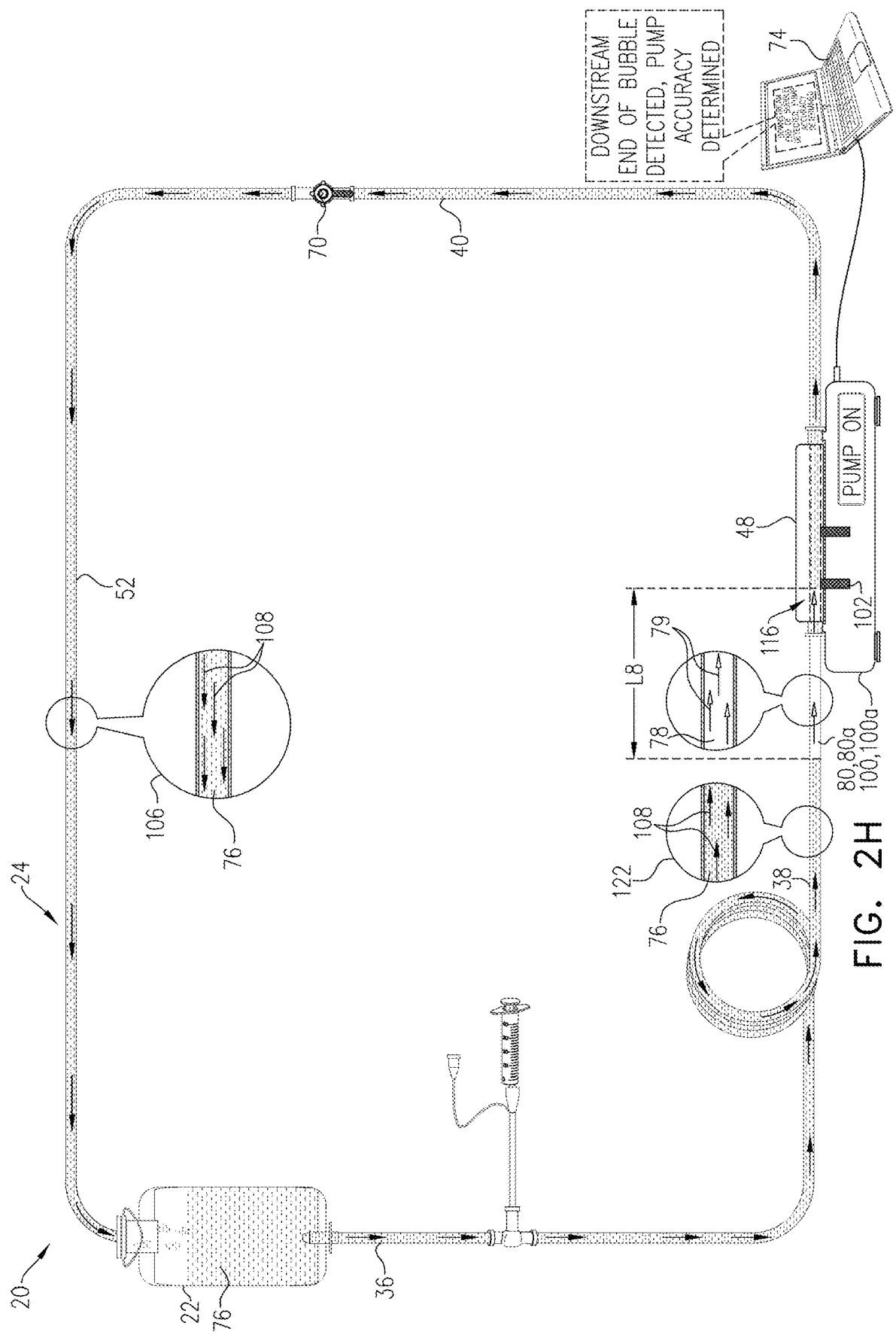

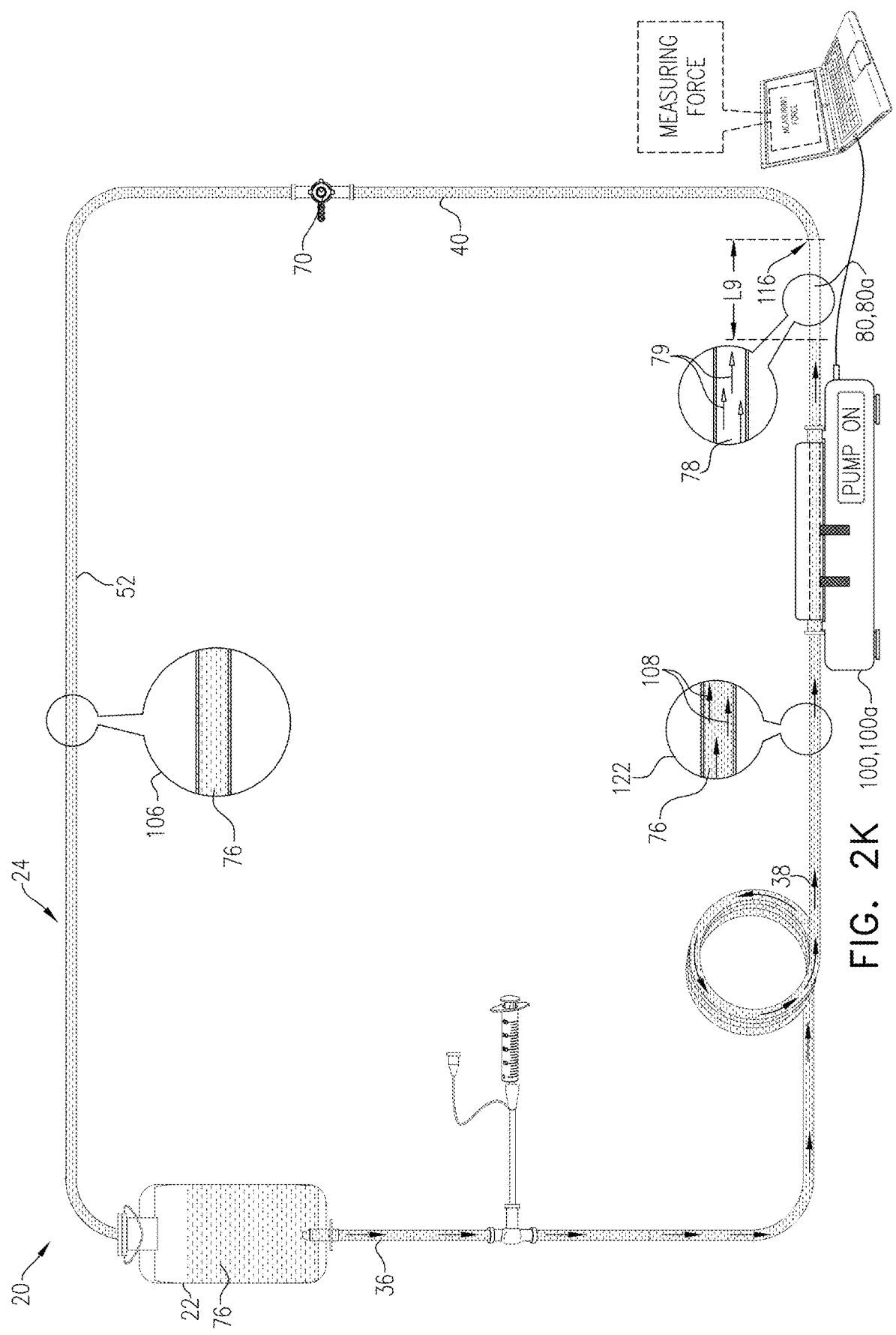

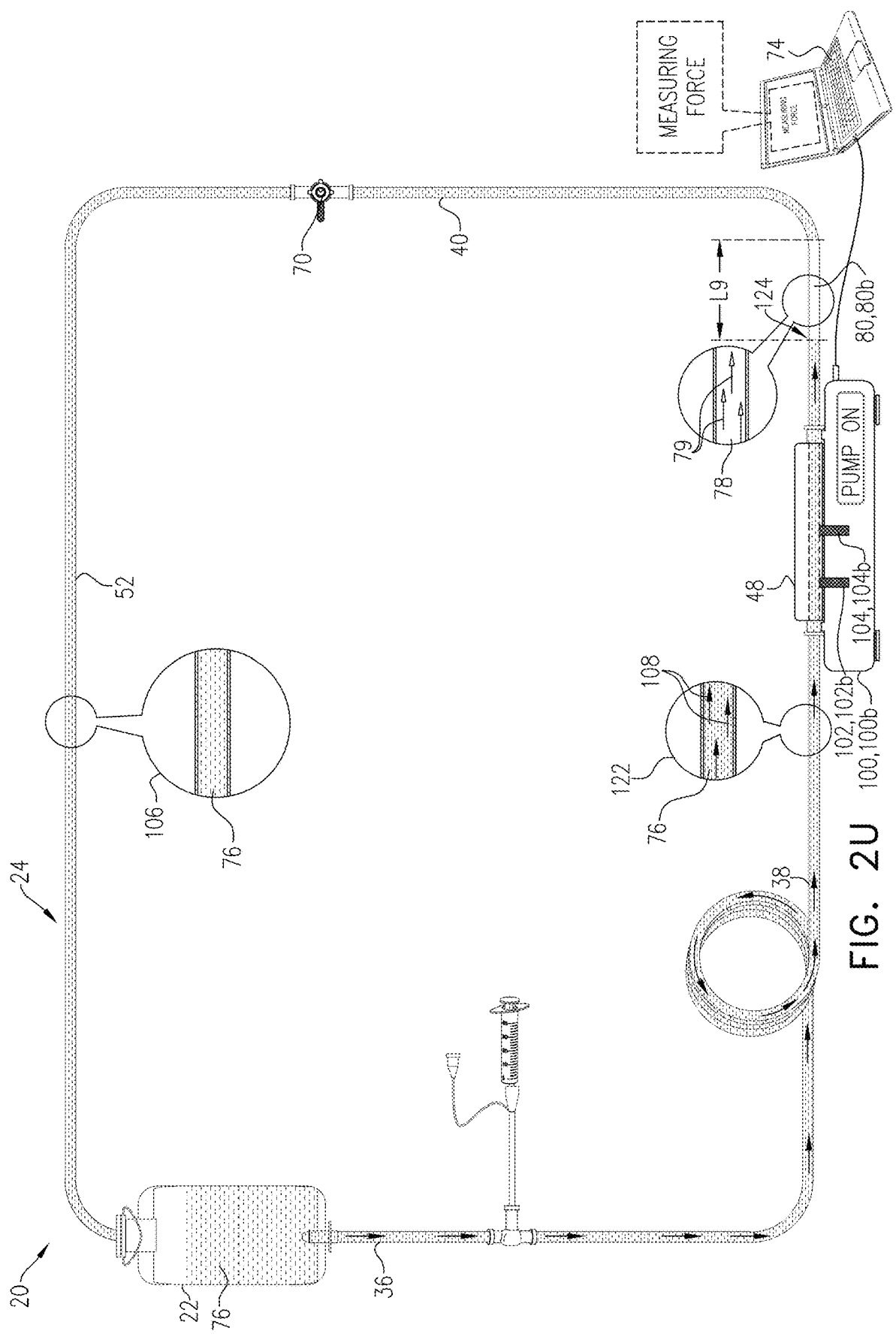

FAST TEST FOR MEDICAL PUMP

CROSS-REFERENCE TO RELATED APPLICATIONS

The present application claims the priority of U.S. 62/936,941 to Eitan, filed Nov. 18, 2019, entitled "Fast test for medical pump," which is incorporated herein by reference.

FIELD OF THE INVENTION

The present invention relates generally to medical fluid-delivery devices, and more specifically to calibration testing of medical fluid-delivery pumps.

BACKGROUND

Pumps are often used in the medical industry for delivering fluids, e.g., drugs, or diagnostic fluids, to subjects. It is important that medical pumps be calibrated properly so as to ensure that subjects receiving fluid from such pumps are receiving the correct dosages at the correct flow rates, and that safety features of a pump, such as for example, occlusion detection, are properly working. Thus, medical pumps being used in the field, e.g., in a hospital setting, doctor's office, medical treatment center, or a subject's home, typically undergo periodic calibration testing in order to check for pumps that may need to be recalibrated and/or fixed prior to being put back into use. Typically, such calibration testing is done at an off-site lab by a technician.

U.S. Pat. No. 9,726,167 to Schweitzer describes an infusion pump which may include a native pumping mechanism to drive fluids through a functionally associated conduit, at least one native sensor to sense a physical characteristic of the fluid within the conduit, and computing circuitry having a decalibration test mode to determine whether the infusion pump is decalibrated. The computing circuitry may be adapted to receive output from at least one native sensor during the decalibration test mode. Other embodiments are also described.

SUMMARY OF THE INVENTION

Apparatus and methods are provided for periodically testing a pump, e.g., a medical pump, in order to determine (a) a parameter of the pump, e.g., a level of pumping accuracy of the pump, or the volume of liquid pumped per pumping cycle of the pump, and/or (b) a level of accuracy of a sensor of the pump, e.g., a force sensor of the pump, and/or a bubble detector of the pump.

In accordance with some applications of the present invention, a method is provided for determining a parameter of a pump based on using the pump to pump a predetermined, known, volume of liquid while the pump simultaneously measures the volume of liquid being pumped. The measured volume of liquid pumped may then be compared to the known volume of liquid pumped in order to determine a parameter of the pump, e.g., in order to assess the pumping accuracy of the pump, e.g., whether the pump is pumping the correct volume of fluid per pumping cycle. After placing liquid into a tube set that is coupled to a pump, an air bubble is injected into the tube such that there is a predetermined, known, volume of liquid between the air bubble and the pump. The pump is then activated so as to advance the air bubble to the bubble detector of the pump. While the pump is pumping, the pump automatically measures the volume of liquid that is being pumped, such that when a downstream edge of the bubble is detected by the bubble detector, the entirety of the predetermined volume of fluid has been pumped and the known volume of liquid pumped may be compared with the volume of liquid as measured by the pump in order to determine a parameter of the pump, e.g., a level of pumping accuracy of the pump.

In accordance with some applications of the present invention, a method is provided for determining a level of accuracy of a sensor, e.g., a force sensor, of a pump. After placing liquid into a tube set that is coupled to a pump, an air bubble is injected into the tube, the pump is activated so as to advance the air bubble past a bubble detector of the pump, while simultaneously measuring the volume of the air bubble. The tube is then occluded downstream of the air bubble and the pump is used to further pump a volume of liquid so as to compress the air bubble. Based on knowing the measured volume of the bubble and the volume of liquid pumped in order to compress the bubble, an expected increase in pressure in the tube is assessed, e.g., calculated. A sensor of the pump, e.g., a force sensor, measures the increase in force in the tube due to the compression of the air bubble, and the expected increase in force may be compared to the measured increase in force in order to determine a level of accuracy of the sensor.

In accordance with some applications of the present invention, a method is provided for determining a parameter of a bubble detector of a pump, e.g., an optical bubble detector. For any given pump, the bubble detector has (a) a pump-specific liquid-signal, e.g., an analog-to-digital (A/D) signal of a specific value, when the bubble detector detects liquid, and (b) a pump-specific air signal, e.g., an A/D signal of a specific value, when the bubble detector detects air. If the bubble detector of a pump is in good working condition, e.g., is properly calibrated, then, while the pump is in use, (a) the values of the liquid-signals generated by the bubble detector when liquid is passing the bubble detector should typically fall within a predetermined range of values that is typically within a delta of +/−30 from the pump-specific liquid-signal, e.g., 30 out of 1024 for a 10-bit A/D signal, and (b) the values of the air-signals generated by the bubble detector when air is passing the bubble detector should typically fall within a predetermined range of values that is typically within a delta of +/−20 from the pump-specific air signal, e.g., 20 out of 1024 for a 10-bit A/D signal.

The inventor has realized that if a bubble detector that is in good working condition, e.g., is properly calibrated, happens to generate a signal (either a liquid-signal or an air-signal) that is outside of the respective expected predetermined range, that signal can be ignored as it is likely not due to a problem with the sensor, but rather a measurement error (e.g., a data transfer error). Correspondingly, it is highly unlikely for a bubble detector that is not in working order, e.g., not properly calibrated, to "accidentally" generate a signal that is within the expected predetermined range. Thus, for example, if a given bubble detector generates a liquid-signal having a value that is within the respective predetermined range, but generates an air-signal having a value that is not within the respective predetermined range, it can still be assumed that the bubble detector is in working order, and that likely an unrelated circumstance caused the air-signal to be out of range. The same is true vice versa, i.e., if a given bubble detector generates an air-signal having a value that is within range, but a liquid-signal that is out of range, it can still be assumed that the bubble detector is in working order. This assumption is further substantiated by the successful completion of the rest of the test, further described hereinbelow, as the measurement of the air bubble size and the calculated pressure all depend on the bubble detector being in good working order.

After placing liquid into a tube set that is coupled to a pump, an air bubble is injected into the tube, and the pump is used to advance the air bubble to and past the bubble detector of the pump. A parameter of the bubble detector may be determined by measuring respective values of the liquid-signals generated by the bubble detector as the liquid is passing the bubble detector and air-signals generated by the bubble detector when the bubble is passing the bubble detector. If at least one of the two signals, i.e., if the generated liquid-signal or the generated air-signal, is within the respective predetermined range of values, then a determination may be made that the bubble detector is in working order, e.g., is properly calibrated.

In accordance with some applications of the present invention, a specialized tube set is provided for carrying out the various tests, which are typically carried out in succession, as further described hereinbelow. The tube set includes (a) a reservoir for holding the liquid, e.g., water, (b) an air port for insertion of air into the tube and (c) a tube cartridge for operatively coupling the tube to a pump at a specific location along the tube, such that there is a predetermined distance (which translates to a predetermined volume of liquid when the tube is filled with liquid) between the air port and the pump when the tube set is coupled to a pump, and (d) a tube-occluding element coupled to the tube downstream of the tube cartridge for occluding liquid flow within the tube. Thus, when the air bubble is injected into the tube, there is a predetermined volume of liquid between the air bubble and the pump.

An air bubble may be injected into the tube and the pump may be used to pump the predetermined volume of liquid between the air bubble and the pump, while simultaneously measuring the volume of the liquid being pumped. When the pump detects the air bubble, as described hereinabove, the known volume of liquid pumped is compared to the measured volume in order to determine a parameter of the pump. The pump is then used to continue advancing the same air bubble past the pump in order to measure a volume of the air bubble. After the air bubble is past the pump, the tube is occluded downstream of the air bubble and the pump is used to pump a further volume of liquid so as to compress the air bubble. As described hereinabove, a sensor of the pump, e.g., a force sensor, measures the increase in force in the tube due to the compression of the air bubble, and an expected increase in force may be compared to the measured increase in force in order to determine a level of accuracy of the sensor. At any point during the advancing of the air bubble through the tube set, liquid-signals and air-signals generated by the bubble detector are measured in order to determine a parameter of the bubble detector. Thus, by moving a single air bubble through the tube set, all three of the abovementioned calibration tests may be performed for a given pump.

Dimensions of the tube set are typically set such that the length of the tube segment that is disposed between the pump and the tube-occluding element is longer than the length of the tube segment that is between the air port and the reservoir. When the air bubble is injected into the tube, the length of the air bubble typically spans the entire length of tube between the air port and the reservoir. The length of the tube segment between the pump and occluding element being longer than the length of the tube segment between the air port and the reservoir allows for the pump to be able to advance the entirety of the air bubble past the pump while the tube-occluding element remains downstream of the air bubble.

Additionally, dimensions of the tube set are typically set such that the length of tube segment that is disposed between the pump and the tube-occluding element is shorter than the length of the tube segment between the air port and the pump. After a given pump is coupled to the tube segment and the abovementioned tests performed, the pump may be disconnected from the tube set and another pump coupled to the tube set in its place. The air bubble, following having been used in performing the tests on the first pump, is typically still in the tube set, between the pump and the tube-occluding element. The length of the tube segment between the pump and the tube-occluding element being shorter than the length of the tube segment between the air port and the pump ensures that as a second bubble is advanced from the air port to the pump, the entirety of the first air bubble that was disposed between the pump and the tube-occluding element will have advanced past the occluding element. Thus, the first air bubble remains within the tube set during the testing of the next pump, yet the first air bubble has no effect on the tests being performed on the next pump—it will simply advance through the tube set as the next pump is tested, typically making its way back to the reservoir where it exits the tube.

There is therefore provided, in accordance with some applications of the present invention, a method for use with a pump, the method including:

placing liquid in a tube that is coupled to the pump;

creating an air bubble in the tube by injecting air into the tube in a manner that does not increase pressure within the tube;

using the pump to measure a volume of the air bubble;

subsequently, occluding the tube downstream of the air bubble;

using the pump, increasing pressure within the tube by pumping a volume of liquid;

using the pump to measure the volume of liquid pumped;

assessing the increase in pressure within the tube based on the measured volume of liquid pumped and the measured volume of the air bubble;

using a sensor of the pump, measuring a sensed increase in pressure in the tube in response to the pumping of the volume of liquid; and based on (i) the assessed increase in pressure and (ii) the sensed increase in pressure, determining a level of accuracy of the sensor.

For some applications, injecting the air into the tube includes injecting the air into the tube at a location that is upstream of the pump.

For some applications, occluding the tube downstream of the air bubble includes occluding the tube downstream of the pump.

For some applications, using the pump to measure the volume of the air bubble includes using the pump to advance the air bubble to, and past, a bubble detector of the pump.

For some applications, using the pump to measure the volume of the air bubble includes assessing the number of pumping cycles of the pump during the advancing of the air bubble past the bubble detector.

For some applications, assessing includes counting an integer number of pumping cycles of the pump.

For some applications, assessing includes assessing a non-integer number of pumping cycles of the pump.

There is further provided, in accordance with some applications of the present invention, a method for use with a pump, the method including:

placing liquid in a tube that is coupled to the pump;

creating an air bubble in the tube by injecting air into the tube in a manner that does not increase pressure within the tube, such that there is a predetermined volume of liquid between the air bubble and the pump;

using the pump to advance the air bubble along the tube to the bubble detector;

using the pump, measuring the volume of liquid pumped to advance the air bubble to the bubble detector; and determining a parameter of the pump based on the measured volume.

For some applications, measuring the volume of liquid pumped to advance the air bubble to the bubble detector includes assessing the number of pumping cycles during which the pump advances the air bubble to the bubble detector.

For some applications, assessing includes counting an integer number of pumping cycles of the pump.

For some applications, assessing includes assessing a non-integer number of pumping cycles of the pump.

For some applications, determining the parameter of the pump includes determining a level of pumping accuracy of the pump.

For some applications, determining the parameter of the pump includes determining a volume of the liquid that is pumped per pumping cycle of the pump.

For some applications, the method further includes:

measuring a value of an air-signal generated by the bubble detector in response to the bubble detector detecting the air bubble; and determining if a value of the air-signal is within a predetermined range of values for detection of an air bubble.

For some applications, measuring the value of the air-signal includes measuring the value of an analog-to-digital (A/D) air signal generated by the bubble detector in response to the bubble detector detecting the air bubble.

For some applications, the method further includes:

measuring a value of a liquid-signal generated by the bubble detector in response to the bubble detector detecting the liquid in the tube; and determining if a value of the liquid-signal is within a predetermined range of values for detection of liquid.

For some applications, measuring the value of the liquid-signal includes measuring the value of an analog-to-digital (A/D) liquid signal generated by the bubble detector in response to the bubble detector detecting the liquid in the tube.

For some applications, the method further includes:

measuring a value of an air-signal generated by the bubble detector in response to the bubble detector detecting the air bubble; and determining if a value of the air-signal is within a predetermined range of values for detection of an air bubble.

For some applications, measuring the value of the air-signal includes measuring the value of an analog-to-digital (A/D) air signal generated by the bubble detector in response to the bubble detector detecting the air bubble.

For some applications, using the pump to advance the air bubble along the tube to the bubble detector includes using the pump to advance the air bubble through a length of the tube that is 20-200 cm long.

For some applications, using the pump to advance the air bubble along the tube to the bubble detector includes using the pump to advance the air bubble from a location that is at a height of 0-100 cm above the pump, with respect to the direction of gravity.

For some applications, using the pump to advance the air bubble to the pump includes maintaining the air bubble between the height of the location above the pump and the pump, with respect to gravity during the advancing.

There is further provided, in accordance with some applications of the present invention, a method for use with a pump, the method including:

placing liquid in a tube that is coupled to the pump;

creating an air bubble in the tube by injecting air into the tube;

using the pump to advance the air bubble along the tube to a bubble detector of the pump;

measuring:
(a) a value of a liquid-signal generated by the bubble detector in response to the bubble detector detecting the liquid within the tube, and
(b) a value of an air-signal generated by the bubble detector in response to the bubble detector detecting the air bubble within the tube;

determining if at least one of the measured values is within a respective predetermined range of values; and determining a parameter of the bubble detector based on the determination.

For some applications, (a) measuring the value of the liquid signal includes measuring the value of an analog-to-digital (A/D) liquid-signal generated by the bubble detector in response to the bubble detector detecting the liquid within the tube, and (b) measuring the value of the air signal includes measuring the value of an A/D air-signal generated by the bubble detector in response to the bubble detector detecting the air bubble within the tube.

There is further provided, in accordance with some applications of the present invention, a method for use with a pump, the method including:

(A) placing liquid in a tube that is coupled to the pump;
(B) creating an air bubble in the tube by injecting air into the tube (a) in a manner that does not increase pressure within the tube, and (b) such that there is a predetermined volume of liquid between the air bubble and the pump;
(C) using the pump to advance the air bubble along the tube to the bubble detector of the pump;
(D) using the pump, assessing accuracy of the pump by automatically measuring the volume of liquid pumped to advance the air bubble to the bubble detector; and
(E) using the pump to continue advancing the air bubble along the tube, past the bubble detector, and using the pump to measure a volume of the air bubble.

For some applications, automatically measuring the volume of liquid pumped to advance the air bubble to the bubble detector includes automatically assessing the number of pumping cycles during which the pump advances the air bubble to the bubble detector.

For some applications, assessing includes counting an integer number of pumping cycles of the pump.

For some applications, assessing includes assessing a non-integer number of pumping cycles of the pump.

For some applications, assessing accuracy of the pump includes determining a level of pumping accuracy of the pump.

For some applications, assessing accuracy of the pump includes determining a volume of the liquid that is pumped per pumping cycle of the pump.

For some applications, using the pump to advance the air bubble along the tube includes driving the liquid within the tube that is downstream of the pump to advance along the tube and subsequently exit the tube into a reservoir from which the pump is operatively coupled to pump the liquid.

For some applications, using the pump to continue advancing the air bubble along the tube, past the bubble detector, includes using the pump to continue advancing the air bubble along the tube, past the pump.

For some applications, using the pump to measure the volume of the air bubble includes using the bubble detector of the pump to measure the volume of the air bubble.

For some applications, using the pump to measure the volume of the air bubble includes assessing the number of pumping cycles of the pump during the advancing of the air bubble past the bubble detector of the pump.

For some applications, assessing includes counting an integer number of pumping cycles of the pump.

For some applications, assessing includes assessing a non-integer number of pumping cycles of the pump.

For some applications, the method further includes: measuring a value of an air-signal generated by the bubble detector in response to the bubble detector detecting the air bubble; and
determining if a value of the air-signal is within a predetermined range of values for detection of an air bubble.

For some applications, measuring the value of the air-signal includes measuring the value of an analog-to-digital (A/D) air signal generated by the bubble detector in response to the bubble detector detecting the air bubble.

For some applications, the method further includes:
measuring a value of a liquid-signal generated by the bubble detector in response to the bubble detector detecting the liquid within the tube; and
determining if a value of the liquid-signal is within a predetermined range of values for the detection of liquid.

For some applications, measuring the value of the liquid-signal includes measuring the value of an analog-to-digital (A/D) liquid signal generated by the bubble detector in response to the bubble detector detecting the liquid in the tube.

For some applications, the method further includes:
measuring a value of an air-signal generated by the bubble detector in response to the bubble detector detecting the air bubble; and
determining if a value of the air-signal is within a predetermined range of values for detection of an air bubble.

For some applications, measuring the value of the air-signal includes measuring the value of an analog-to-digital (A/D) air signal generated by the bubble detector in response to the bubble detector detecting the air bubble.

For some applications, injecting the air into the tube includes injecting the air into the tube at a location that is upstream of the pump.

For some applications, the method further includes:
(F) subsequently, occluding the tube downstream of the air bubble,
(G) using the pump to increase pressure within the tube by pumping a volume of liquid,
(H) using the pump to measure the volume of liquid pumped to increase pressure within the tube;
(I) assessing the increase in pressure within the tube based on (a) the measured volume of liquid pumped to increase the pressure within the tube and (b) the measured volume of the air bubble;

(J) using a sensor of the pump, measuring a sensed increase in pressure in the tube in response to the pumping of the volume of liquid; and
(K) assessing accuracy of the sensor based on the assessed increase in pressure and the sensed increase in pressure.

For some applications, occluding the tube downstream of the air bubble includes occluding the tube downstream of the pump.

For some applications, the pump is a first pump, and wherein the method further includes, subsequently to step (K):
(i) removing the occlusion of the tube,
(ii) disconnecting the first pump from the tube;
(iii) coupling a second pump to the tube; and
(iv) repeating steps (B) through (K) using the second pump.

For some applications, repeating steps (B) through (K) using the second pump includes repeating steps (B) through (K) without repeating step (A) prior to the repeating of steps (B) through (K).

For some applications, repeating steps (B) through (K) using the second pump includes repeating steps (B) through (K) without using the first pump to administer anything to a patient (i) following the completion of step (K) using the first pump and (ii) prior to the coupling of the second pump to the tube.

For some applications, repeating steps (B) through (K) includes using the same tube to repeat steps (B) through (K) 10-50 times using a respective pump each time.

For some applications, the air bubble created in step (B) using the first pump is a first air bubble, and wherein repeating step (B) using the second pump includes creating a second air bubble in the tube while the first air bubble remains within the tube at a location that is downstream of the pump.

For some applications, repeating steps (B) through (E) using the second pump includes driving the first air bubble to advance along the tube, such that repeating step (F) using the second pump comprises occluding the tube downstream of the second air bubble and not downstream of any part of the first air bubble.

For some applications, repeating steps (B) through (E) using the second pump includes driving the first air bubble to advance along the tube and subsequently exit the tube into a reservoir from which the pump is operatively coupled to pump the liquid.

For some applications, using the pump to advance the air bubble along the tube to the bubble detector includes using the pump to advance the air bubble through a length of tube that is 20-200 cm long.

For some applications, using the pump to advance the air bubble along the tube to the bubble detector includes using the pump to advance the air bubble from a location that is at a height of 0-100 cm above the pump, with respect to the direction of gravity.

For some applications, using the pump to advance the air bubble to the pump includes maintaining the air bubble between the height of the location above the pump and the pump, with respect to gravity during the advancing.

There is further provided, in accordance with some applications of the present invention, apparatus for use with a pump, the apparatus including:
a reservoir configured to hold a liquid;
a tube having a first segment, a second segment downstream of the first segment, and a third segment downstream of the second segment, the first segment coupled to the reservoir such that liquid from the reservoir is received within the first segment through an upstream end of the first segment, the tube being configured to be operatively coupled to the pump at a downstream end of the second segment and at an upstream end of the third segment;

an air port coupled to the tube at a downstream end of the first segment and at an upstream of the second segment, such that (a) the first segment of the tube is between the reservoir and the air port and (b) the second segment of the tube is between the air port and the pump when the tube is operatively coupled to the pump, the air port configured to facilitate insertion of an air bubble into the tube, and the second segment of tube defining a predetermined volume of liquid between the air port and the pump when the tube is filled with liquid; and a tube-occluding element coupled to a downstream end of the third segment of the tube, and configured to be used to reversibly occlude the tube, such that a length of the third segment is:

(a) longer than the first segment, and
(b) shorter than the second segment.

For some applications, a length of the first segment of the tube is 2-50 cm.

For some applications, a length of the second segment of the tube is 20-200 cm.

For some applications, the length of the third segment of the tube is 20-80 cm.

For some applications, a length of the third segment of the tube is 20-50% longer than a length of the first segment.

For some applications, the length of the third segment is 20-50% longer than a length of the first segment, and wherein the length of the second segment is 20-80% longer than the length of the third segment.

For some applications, when the tube is operatively coupled to the pump the air port is disposed at a location that is at a height of 0-100 cm above the pump, with respect to gravity during the advancing.

For some applications, when the tube is operatively coupled to the pump the second segment of the tube is maintained between the height of the location above the pump and the pump, with respect to gravity during the advancing.

For some applications, (a) the tube has a fourth segment downstream of the third segment, (b) the tube-occluding element is coupled to an upstream end of the fourth segment and (c) a downstream end of the fourth segment is configured to be coupled to the reservoir such that liquid from the fourth segment is received within the reservoir through the downstream end of the fourth segment.

For some applications, a cap of the reservoir is coupled to the fourth segment of the tube, downstream of the third segment, prior to the tube being packaged for commercial sale such that while the apparatus is disposed within commercial packaging the cap of the reservoir is coupled to the tube.

For some applications, the air port includes a syringe that is coupled to the tube while the apparatus is disposed within commercial packaging.

For some applications, the apparatus further includes a tube cartridge that is fixed to the tube and is configured to be operatively coupled to the pump to allow action of the pump to pump fluid through the tube.

There is further provided, in accordance with some applications of the present invention, a computer software product, for use with:

a pump,
a tube that is coupled to the pump and into which liquid is placed, and
an air bubble that is injected into the tube in a manner that does not increase pressure within the tube, the computer software product including a non-transitory computer-readable medium in which program instructions are stored, which instructions, when read by a computer cause the computer to perform the steps of:

using the pump to measure a volume of the air bubble;
subsequently to the tube being occluded downstream of the air bubble, using the pump, increasing pressure within the tube by pumping a volume of liquid;
using the pump to measure the volume of liquid pumped;
assessing the increase in pressure within the tube based on the measured volume of liquid pumped and the measured volume of the air bubble;
using a sensor of the pump, measuring a sensed increase in pressure in the tube in response to the pumping of the volume of liquid; and
based on (i) the assessed increase in pressure and (ii) the sensed increase in pressure, determining a level of accuracy of the sensor.

There is further provided, in accordance with some applications of the present invention, a computer software product, for use with:

a pump,
a tube that is coupled to the pump and into which liquid is placed, and
an air bubble that is injected into the tube in a manner that does not increase pressure within the tube, and such that there is a predetermined volume of liquid between the air bubble and the pump, the computer software product including a non-transitory computer-readable medium in which program instructions are stored, which instructions, when read by a computer cause the computer to perform the steps of:

using the pump to advance the air bubble along the tube to the bubble detector;
using the pump, measuring the volume of liquid pumped to advance the air bubble to the bubble detector; and
determining a parameter of the pump based on the measured volume.

There is further provided, In accordance with some applications of the present invention, a computer software product, for use with:

a pump,
a tube that is coupled to the pump and into which liquid is placed, and
an air bubble that is injected into the tube, the computer software product including a non-transitory computer-readable medium in which program instructions are stored, which instructions, when read by a computer cause the computer to perform the steps of:

using the pump to advance the air bubble along the tube to a bubble detector of the pump;
measuring:
(a) a value of a liquid-signal generated by the bubble detector in response to the bubble detector detecting the liquid within the tube, and
(b) a value of an air-signal generated by the bubble detector in response to the bubble detector detecting the air bubble within the tube;
determining if at least one of the measured values is within a respective predetermined range of values; and
determining a parameter of the bubble detector based on the determination.

There is further provided in accordance with some applications of the present invention, a computer software product, for use with:
a pump,
a tube that is coupled to the pump and into which liquid is placed, and
an air bubble that is injected into the tube in a manner that does not increase pressure within the tube, and such that there is a predetermined volume of liquid between the air bubble and the pump,
the computer software product including a non-transitory computer-readable medium in which program instructions are stored, which instructions, when read by a computer cause the computer to perform the steps of:
using the pump to advance the air bubble along the tube to the bubble detector of the pump;
using the pump, assessing accuracy of the pump by automatically measuring the volume of liquid pumped to advance the air bubble to the bubble detector; and
using the pump to continue advancing the air bubble along the tube, past the bubble detector, and using the pump to measure a volume of the air bubble.

The present invention will be more fully understood from the following detailed description of applications thereof, taken together with the drawings, in which:

DETAILED DESCRIPTION

Figure 1A:
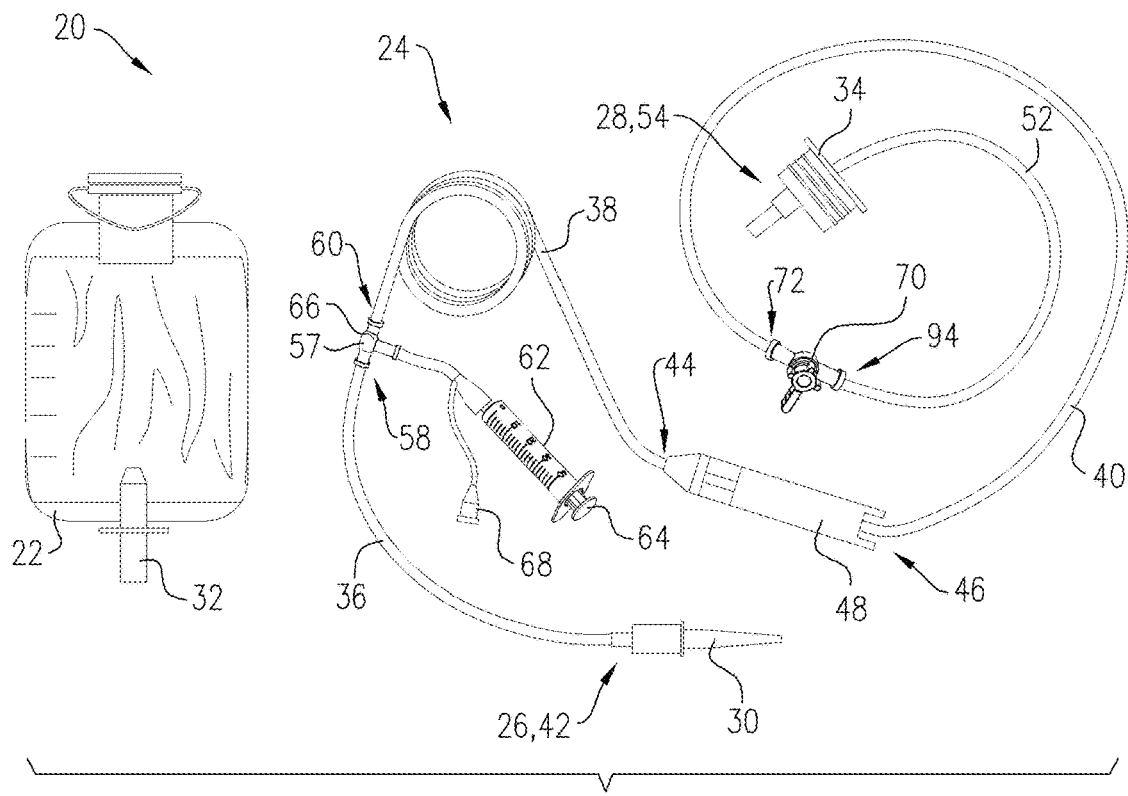
FIGS. 1A-B show a tube set that is for use with a pump, e.g., a medical pump, in accordance with some applications of the present invention.
Figure 1B:
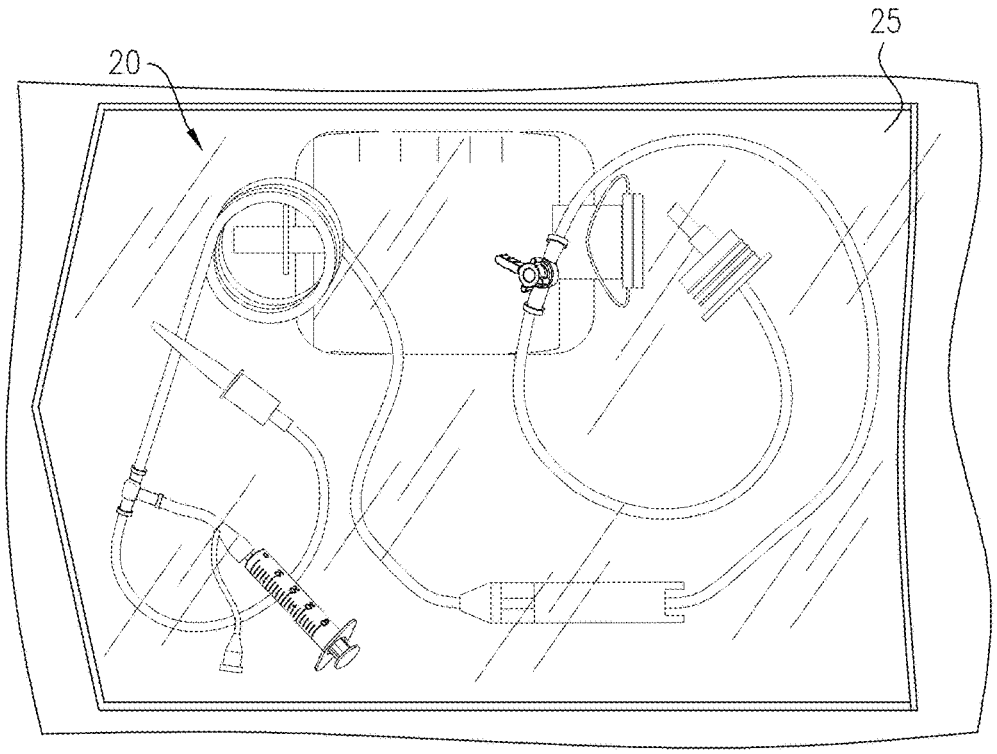
Figure 2A:
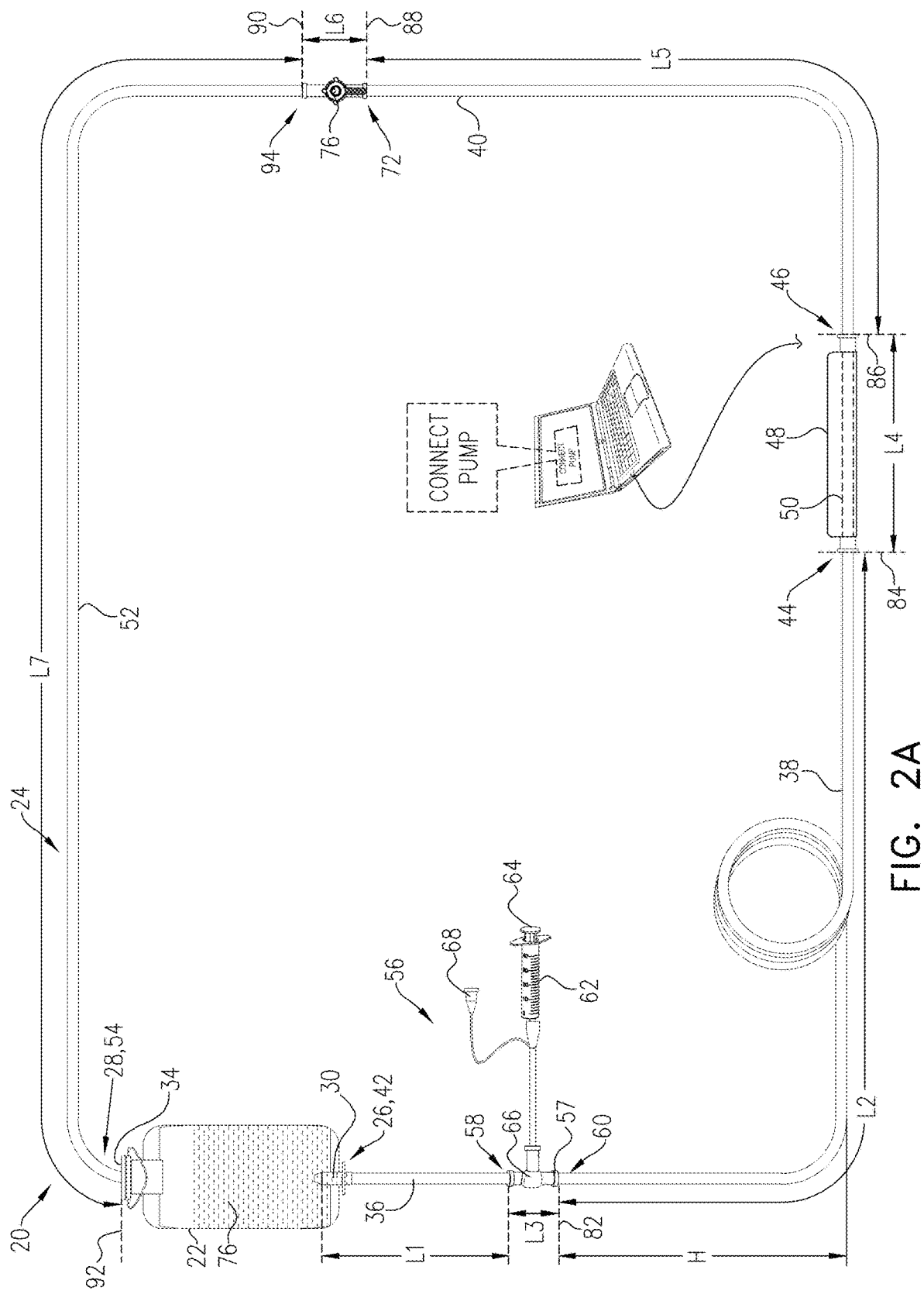
FIGS. 2A-W are schematic illustrations that sequentially illustrate the tube set of FIGS. 1A-B during use, in accordance with some applications of the present invention.
Figure 2B:
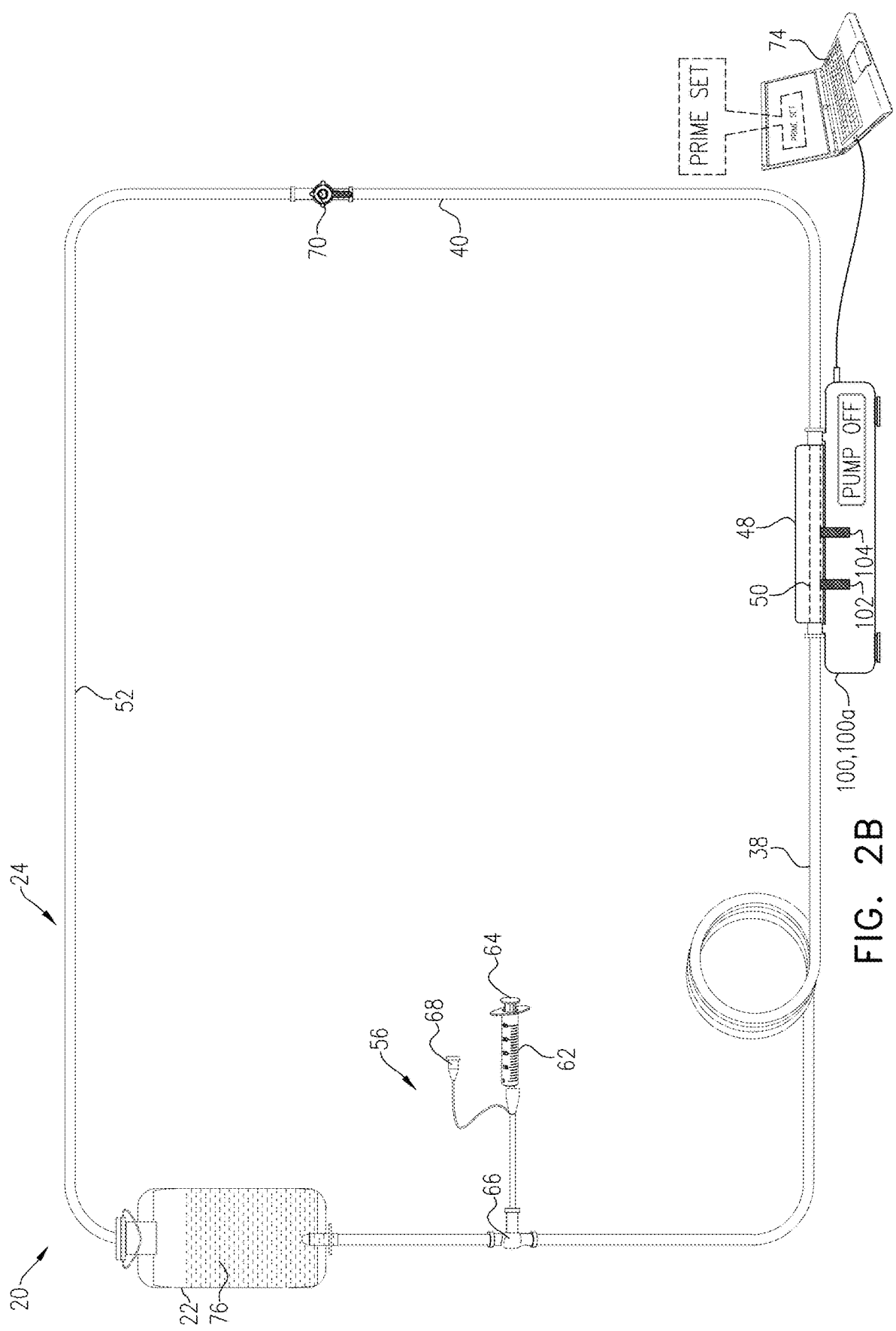

Reference is now made to FIGS. 1A-B, which show a tube set 20 that is for use with a pump, e.g., a medical pump as shown in FIG. 2B, in accordance with some applications of the present invention. Typically, tube set 20 comprises a reservoir 22 for holding a liquid, e.g., water. For some applications, reservoir 22 may be any standard enteral feeding bag. Tube set 20 includes a tube 24 having an upstream end 26 and a downstream end 28. As used throughout the present application, including in the claims, the upstream and downstream ends of a tube segment are defined such that when fluid is flowing through the tube segment, the fluid flows from the upstream end of the tube segment to the downstream end of the tube segment. When tube set 20 is assembled, e.g., by a technician performing the plurality of tests described hereinbelow, both upstream end 26 and downstream end 28 of tube 24 are coupled to reservoir 22. Typically, at upstream end 26 of tube 24 there is a reservoir connector 30 which couples, e.g., is inserted into, an exit spout 32 of reservoir 22. Near downstream end 28 of tube 24, a cap 34 of reservoir 22 is coupled to tube 24, such that when reservoir 22 is closed with cap 34, downstream end 28 of tube 24 is disposed within reservoir 22. For example, cap 34 may be a standard enteral feeding bag cap, with a hole drilled in the cap and tube 24 disposed through the hole. As further described hereinbelow, the calibration test performed using tube set 20 may be performed consecutively for multiple pumps. Having downstream end 28 of tube 24 return the fluid to reservoir 22 enables (i) the setup to remain identical for each test performed and (ii) recirculating of the fluid. As each pump is tested, fluid advances through tube set 20 during the test and cycles back to the reservoir.

Typically, cap 34 of reservoir 22 is coupled to tube 24 prior to tube 24 being packaged for commercial sale, i.e., cap 34 is coupled to tube 24 in commercial packaging 25. When tube set 20 is removed from commercial packaging 25, e.g., by the technician who is testing the pumps, reservoir 22 is filled with liquid, e.g., water, upstream end 26 of tube 24 is coupled to reservoir 22 via reservoir connector 30, and cap 34 used to close reservoir 22, thereby coupling downstream end 28 of tube 24 to reservoir 22.

Tube 24 of tube set 20 typically has at least four tube segments. A first segment 36, a second segment 38 downstream of first segment 36, a third segment 40 downstream of second segment 38, and a fourth segment 52 downstream of third segment 40. In use, first segment 36 is coupled to reservoir 22 (e.g., via reservoir connector 30 as described hereinabove) such that liquid from reservoir 22 is received within first segment 36 through an upstream end 42 of first segment 36. Tube 24 is operatively coupled to a pump at a downstream end 44 of second segment 38 and at an upstream end 46 of third segment 40. Typically, tube 24 is operatively coupled to the pump via a tube cartridge 48, through which is disposed a pump segment 50 of tube 24, pump segment 50 of tube 24 being between second segment 38 and third segment 40. Tube cartridge 48 is coupled to tube 24 at a fixed location along tube 24.

Fourth segment 52 typically leads back to reservoir 22 when tube set 20 is assembled, such that liquid 76 from fourth segment 52 is received within reservoir 22 through downstream end 54 of fourth segment 52. Cap 34 of reservoir 22 is typically coupled to fourth segment 52 of tube 24 at a downstream end 54 of fourth segment 52. Alternatively, for some applications, downstream end 28 of tube 24 may not lead back to reservoir 22, but rather may be set up to drain into an external receptacle as liquid is advanced through tube set 20.

An air port 56 is coupled to tube 24, typically via a connector 57, e.g., a Y-connector or a T-connector, at downstream end 58 of first segment 36 and at upstream end 60 of second segment 38, such that (a) first segment 36 of tube 24 is between reservoir 22 and air port 56 and (b) second segment 38 of tube 24 is between air port 56 and the pump when tube 24 is operatively coupled to the pump. For some applications, air port 56 includes (i) a syringe 62, (ii) a plunger 64 disposed within the barrel of syringe 62, (iii) a first one-way valve 66 positioned so as to allow fluid, e.g., air, to flow from air port 56 into first segment 36 of tube 24, and a second one-way valve 68 positioned so as to allow air from the external environment into air port 56, i.e., into syringe 62. Thus, air port 56 facilitates insertion of an air bubble into tube 24, i.e., into first segment 36 of tube 24, as further described hereinbelow with reference to FIGS. 2E-F. Typically, syringe 62 is coupled to tube 24 while tube set 20 is disposed within commercial packaging 25.

A tube-occluding element 70, e.g., a valve, is coupled to a downstream end 72 of third segment 40 and an upstream end 94 of fourth segment 52. Tube-occluding element 70 is used to reversibly occlude tube 24, e.g., by toggling the valve between open and closed positions, or sliding a clamp on and off tube 24.

Figure 2C:
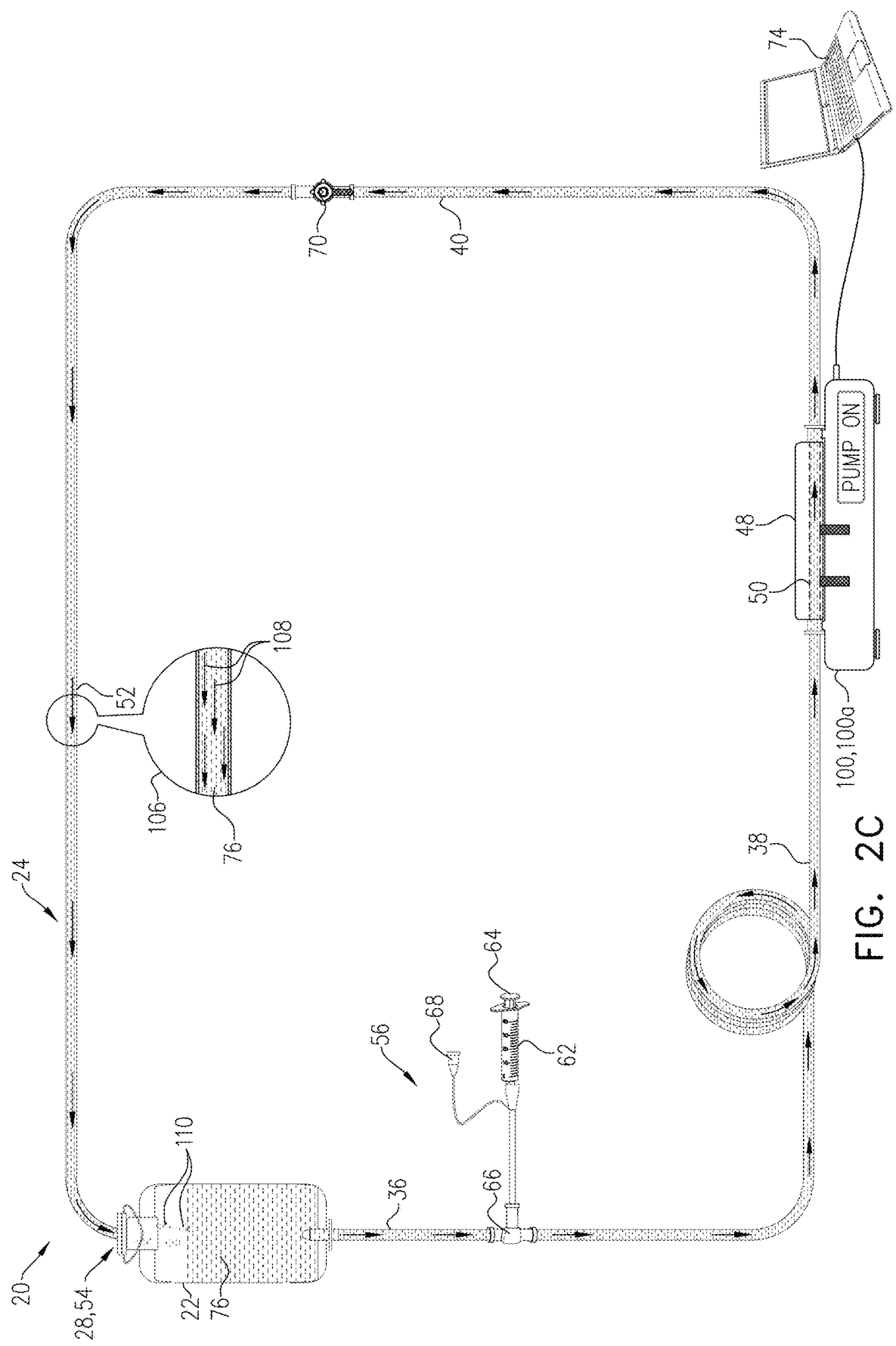
Figure 2D:
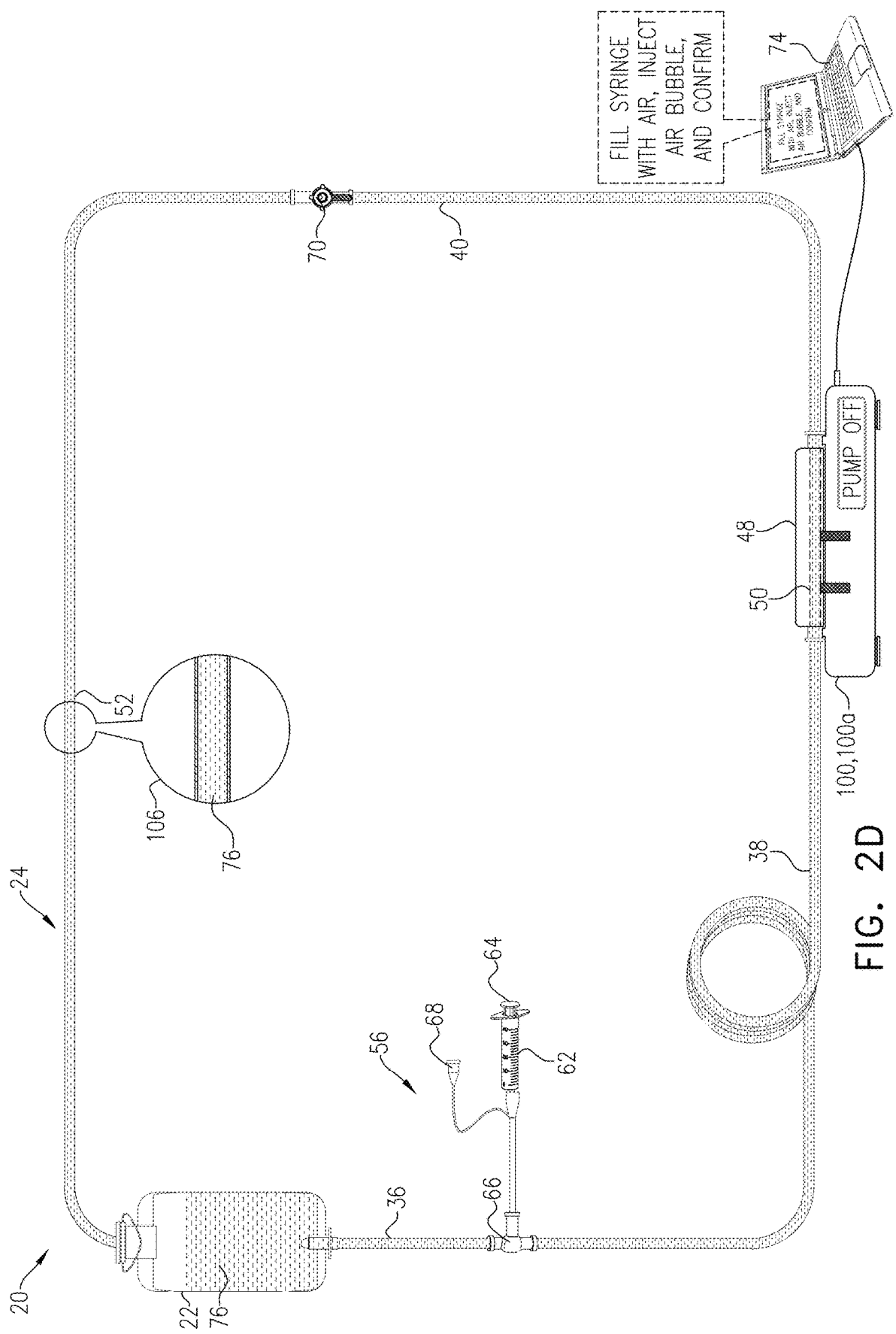
Figure 2E:
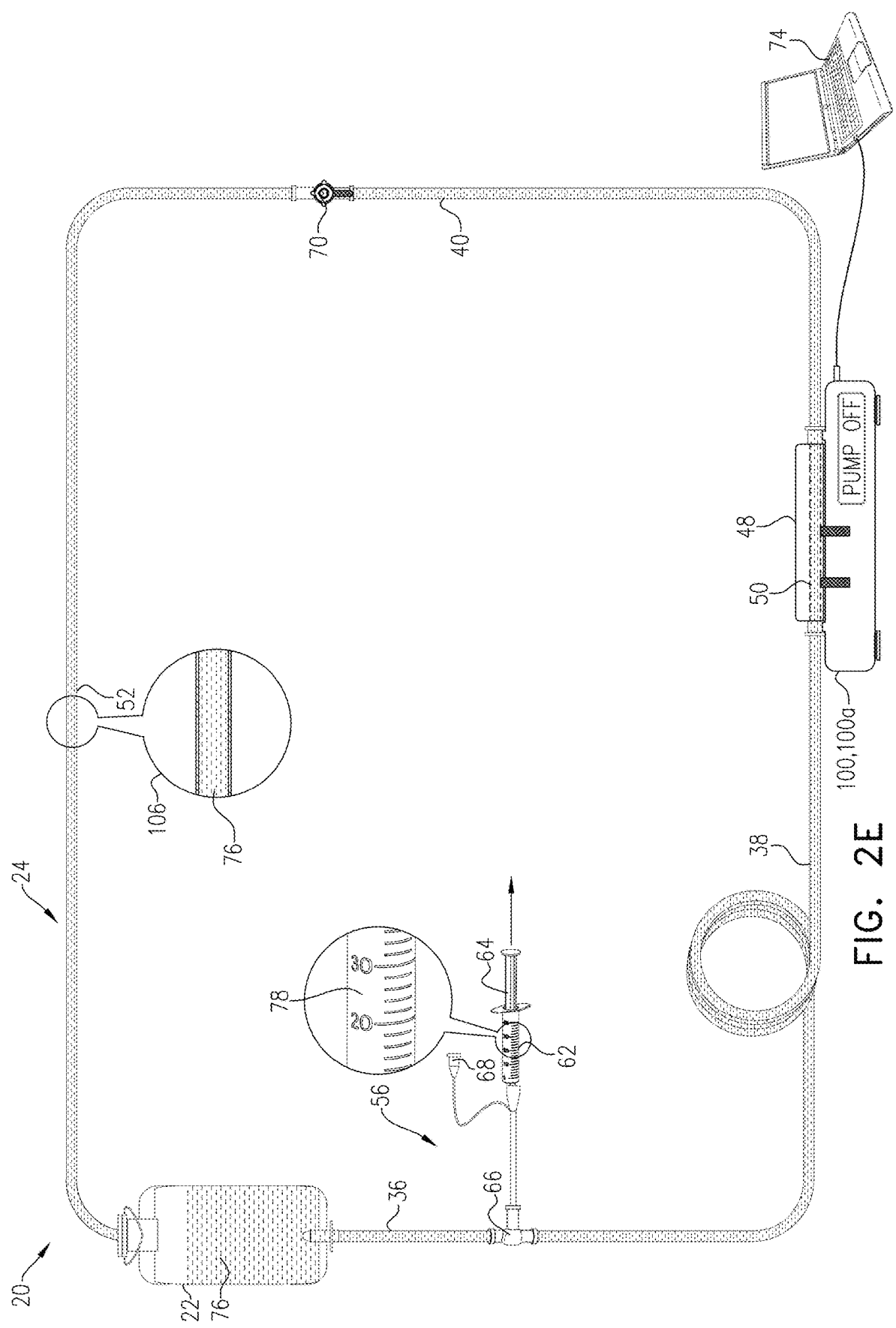
Figure 2F:
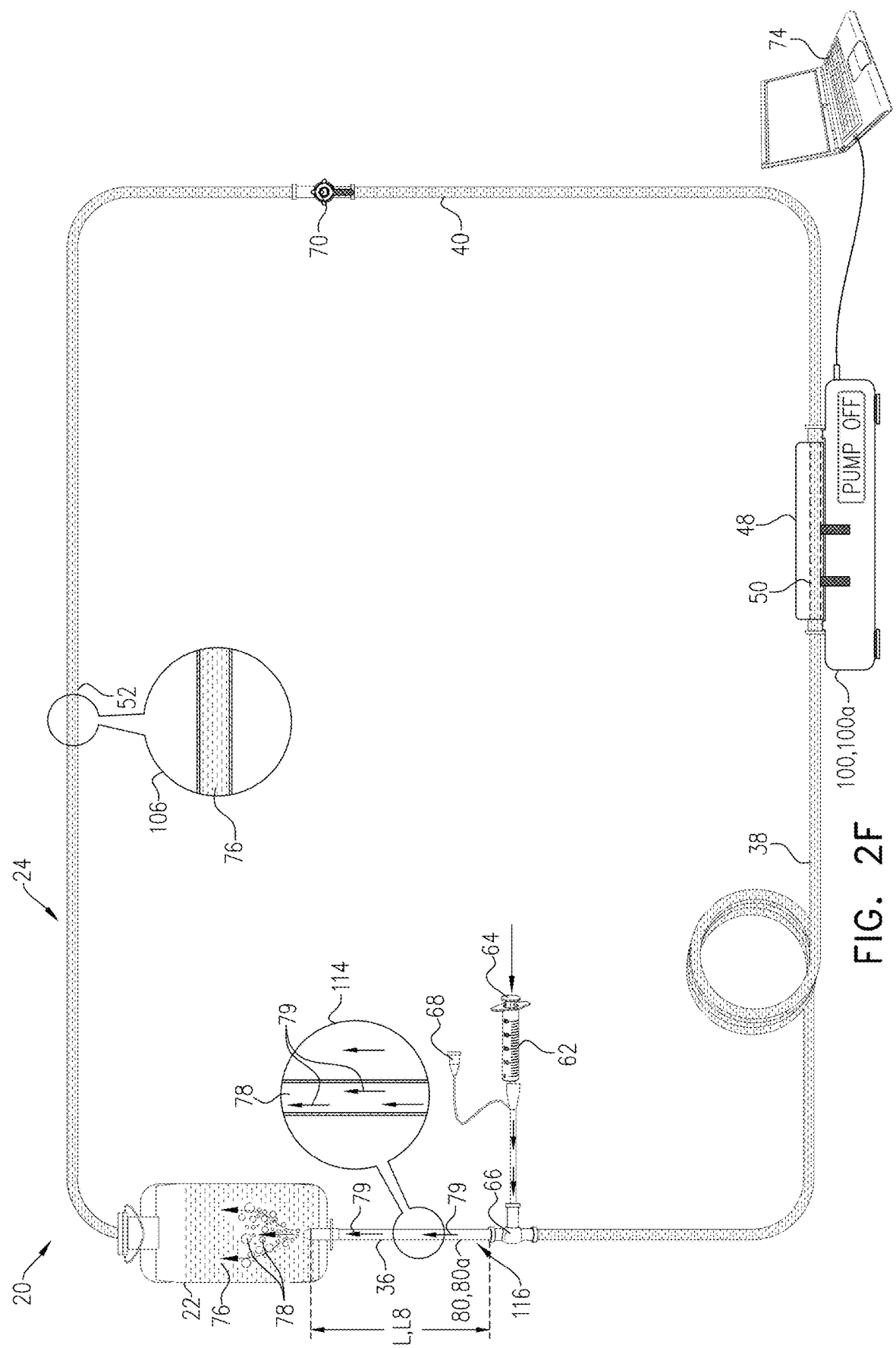
Figure 2G:
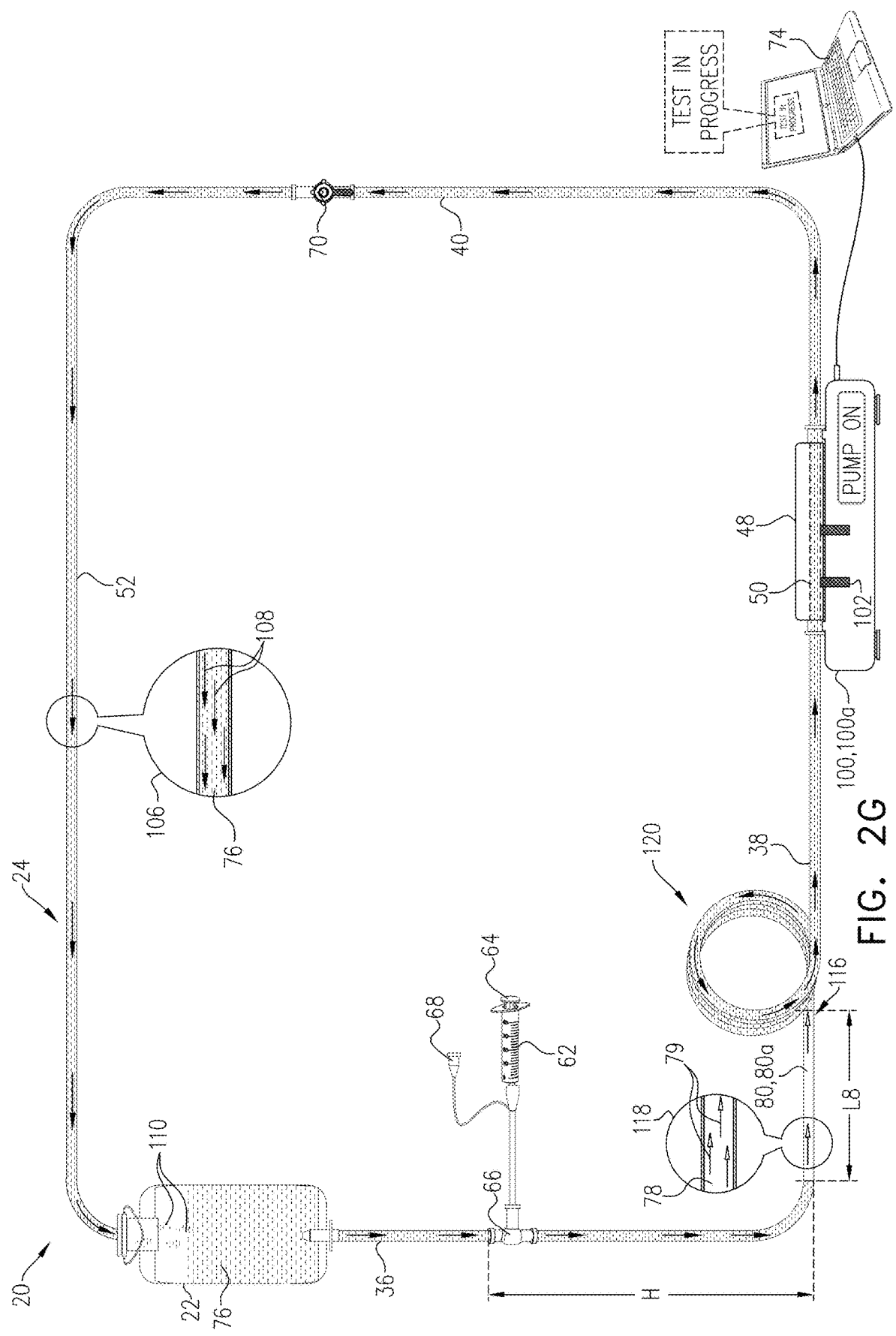
Figure 21:
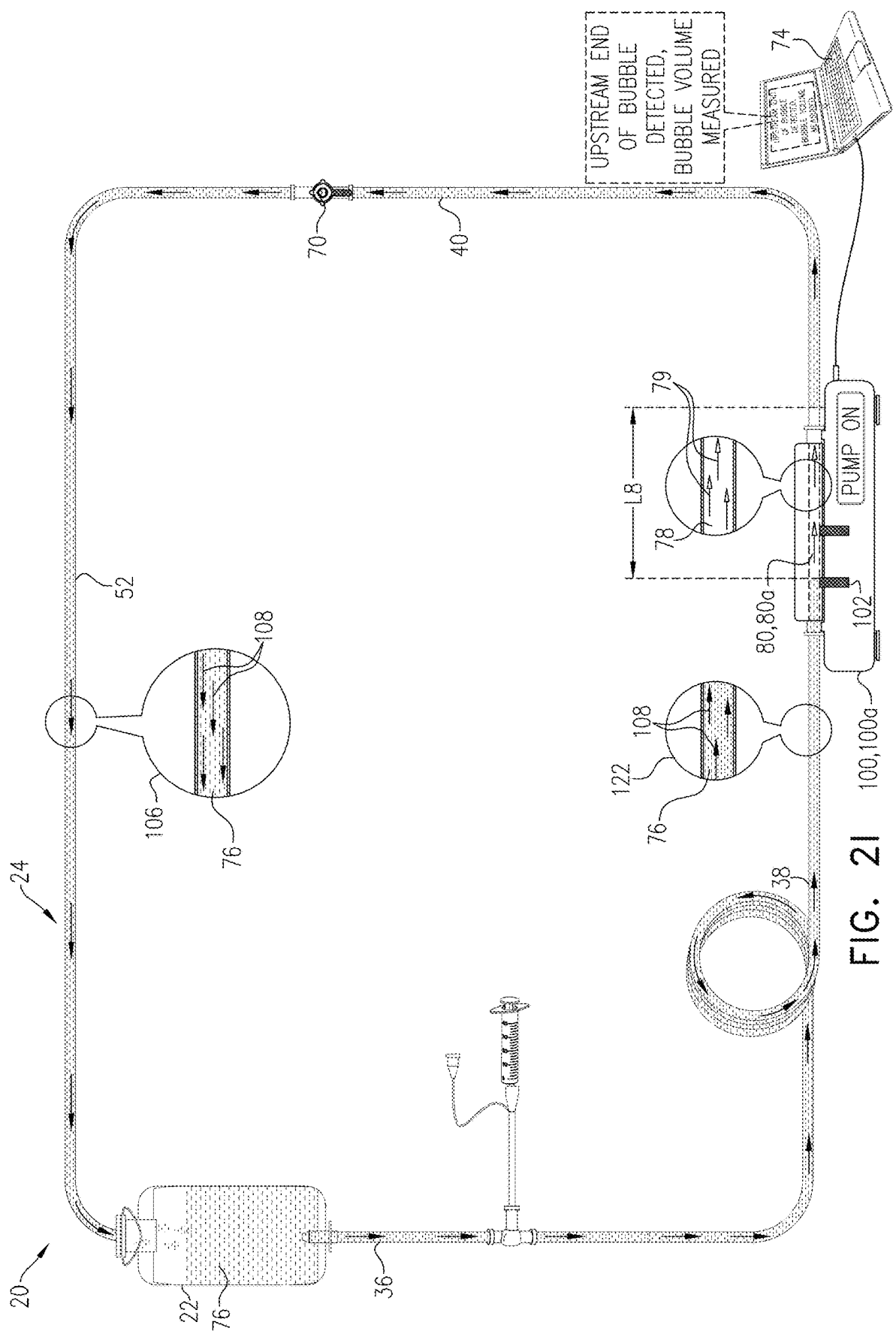
Figure 2J:
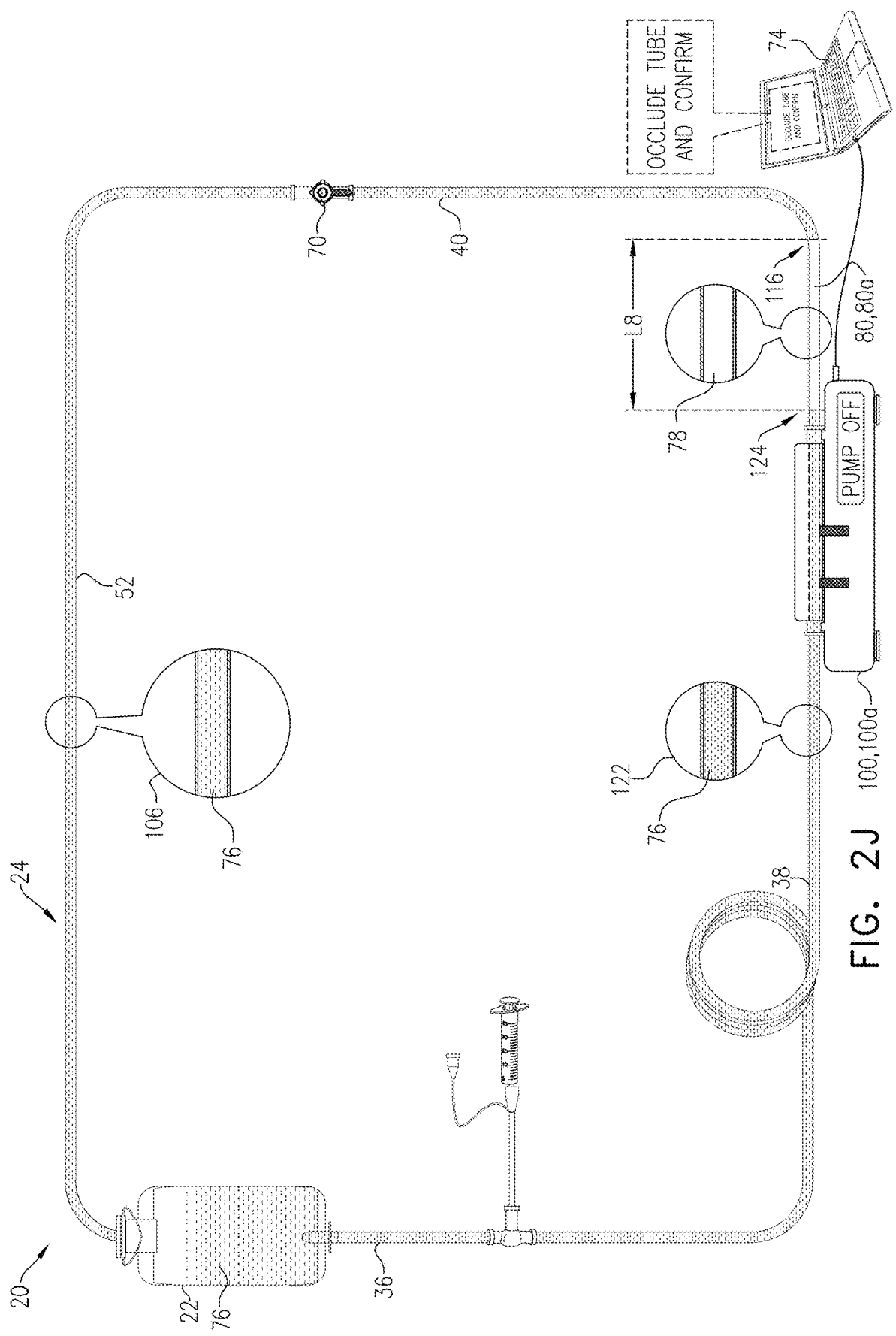
Figure 2L:
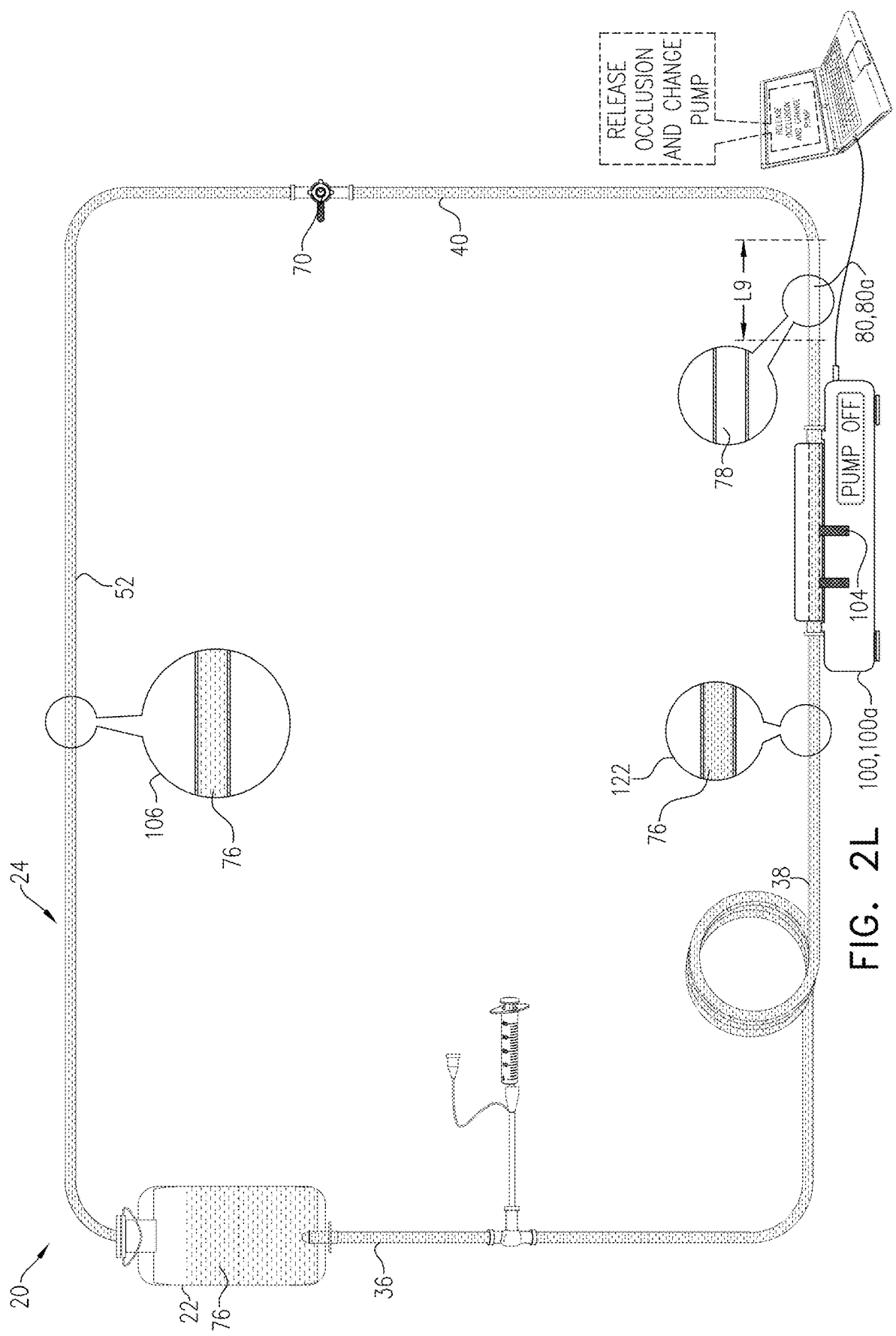
Figure 2M:
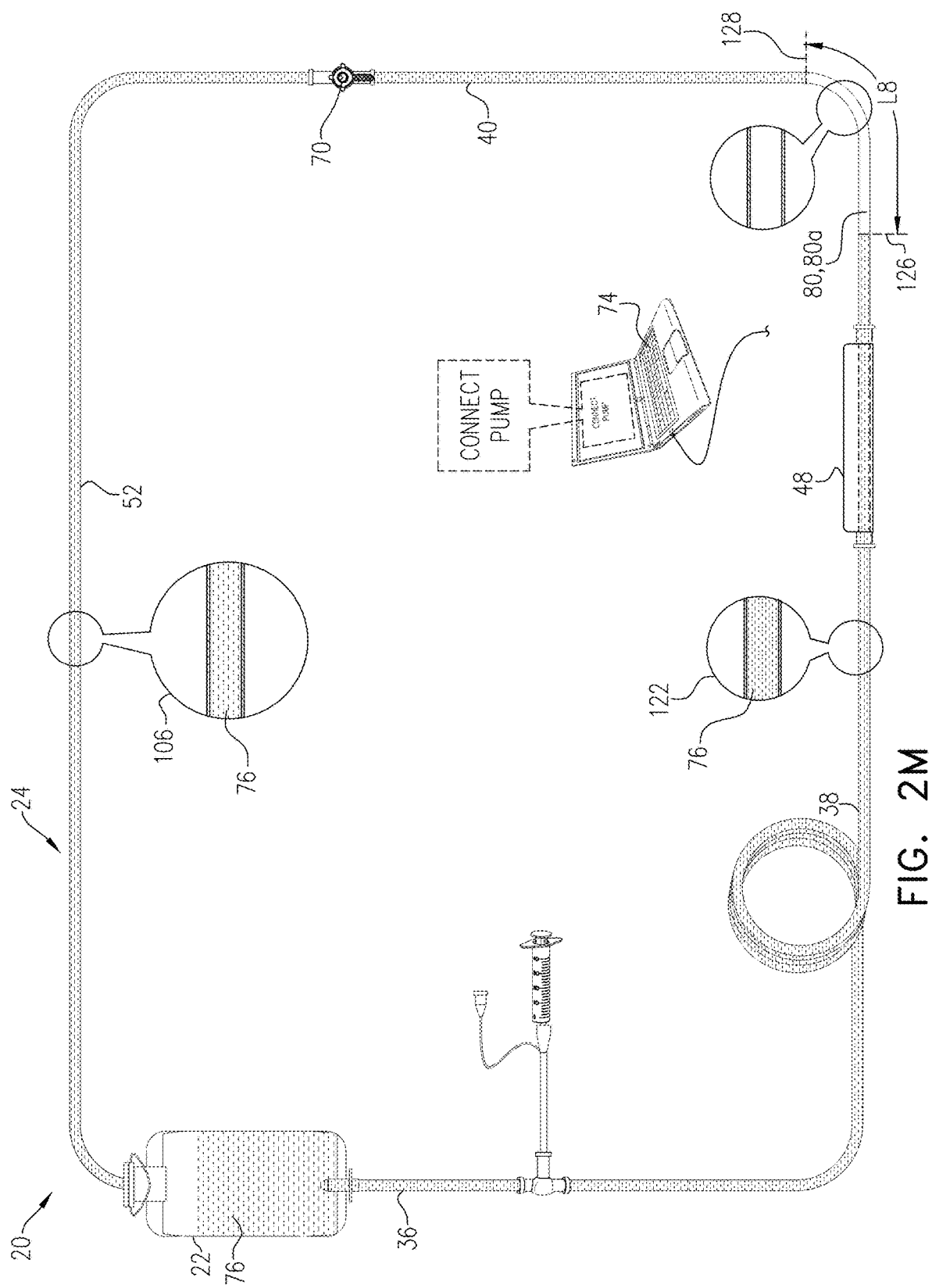
Figure 2N:
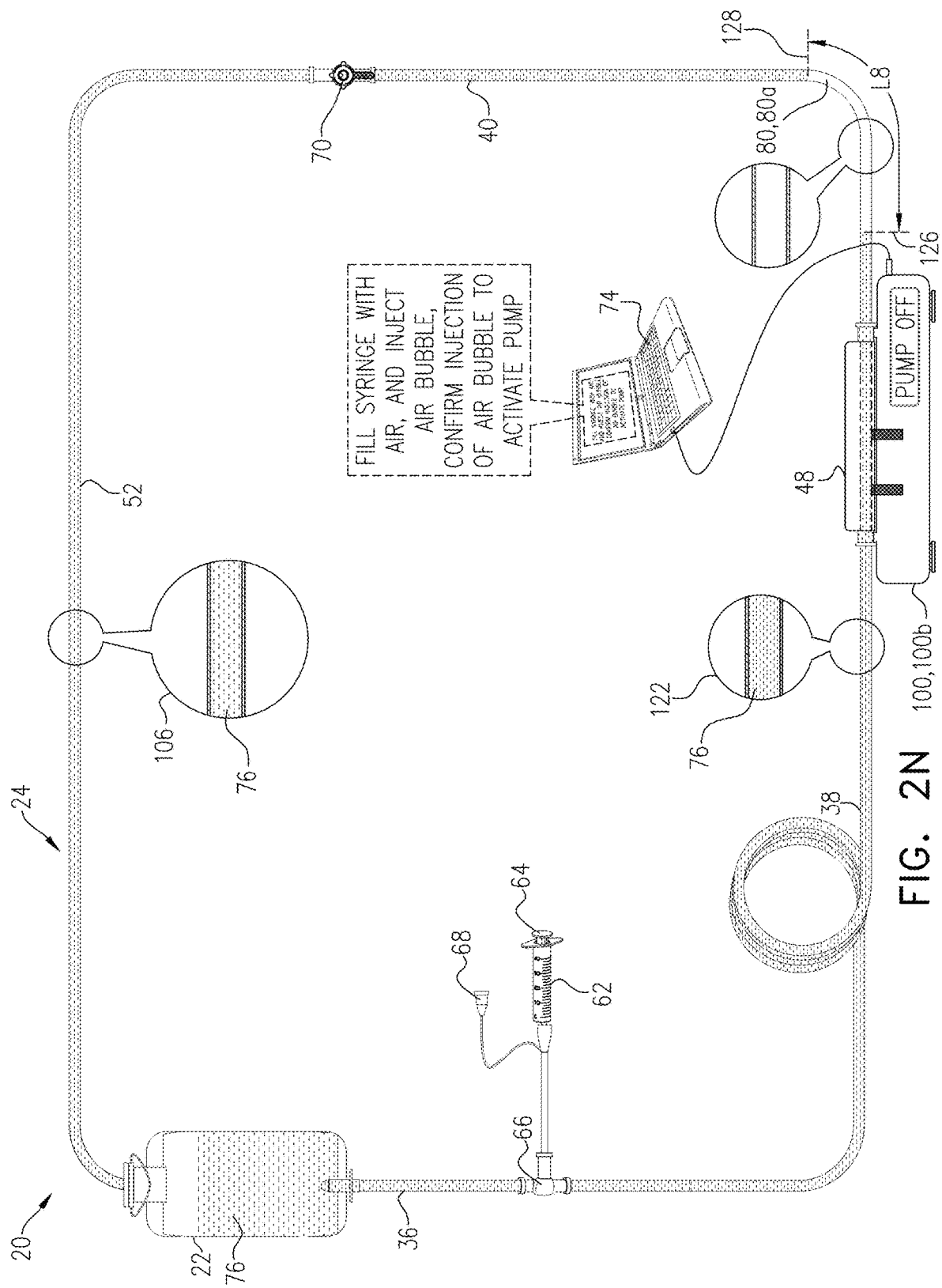
Figure 20:
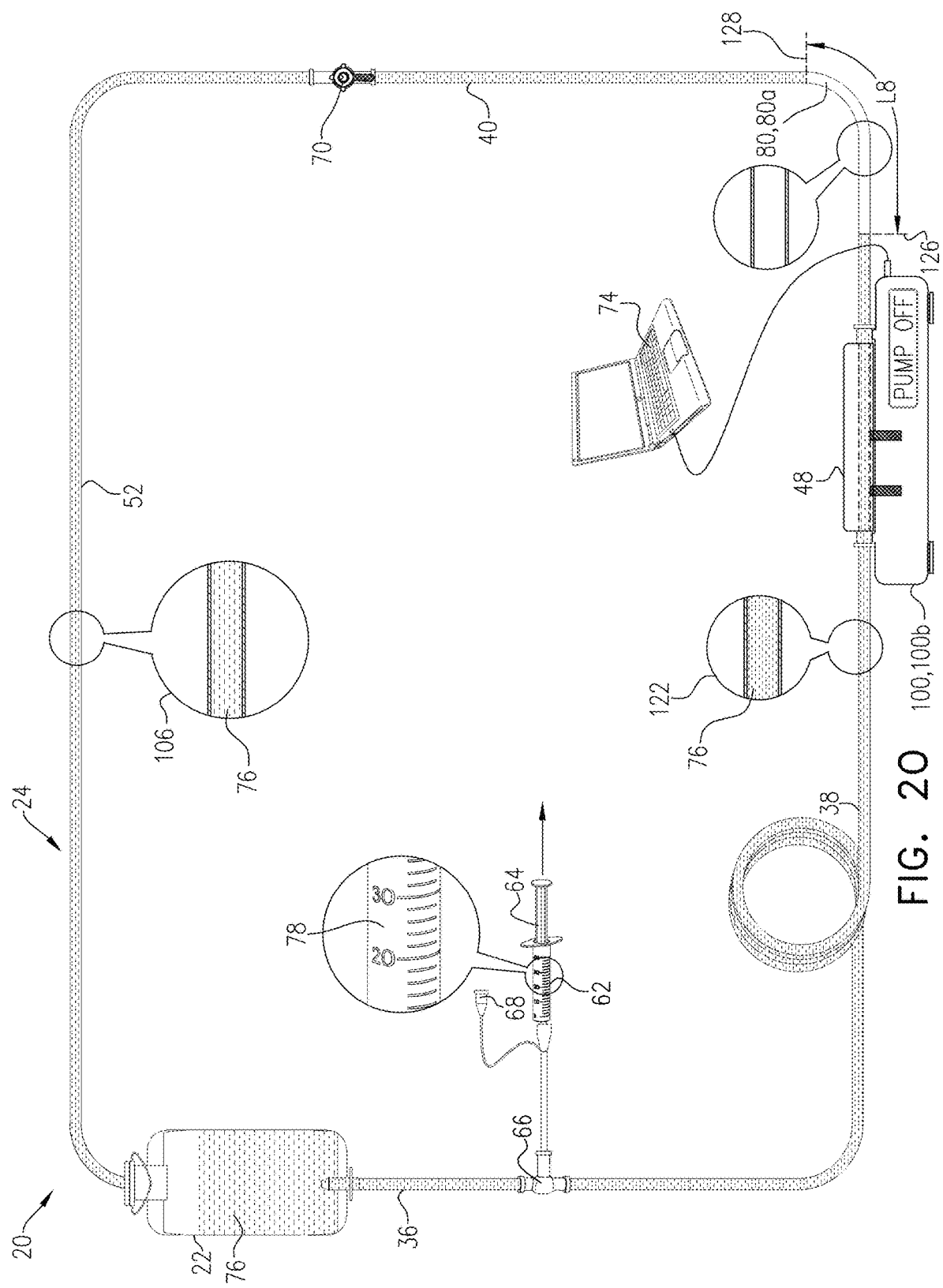
Figure 2P:
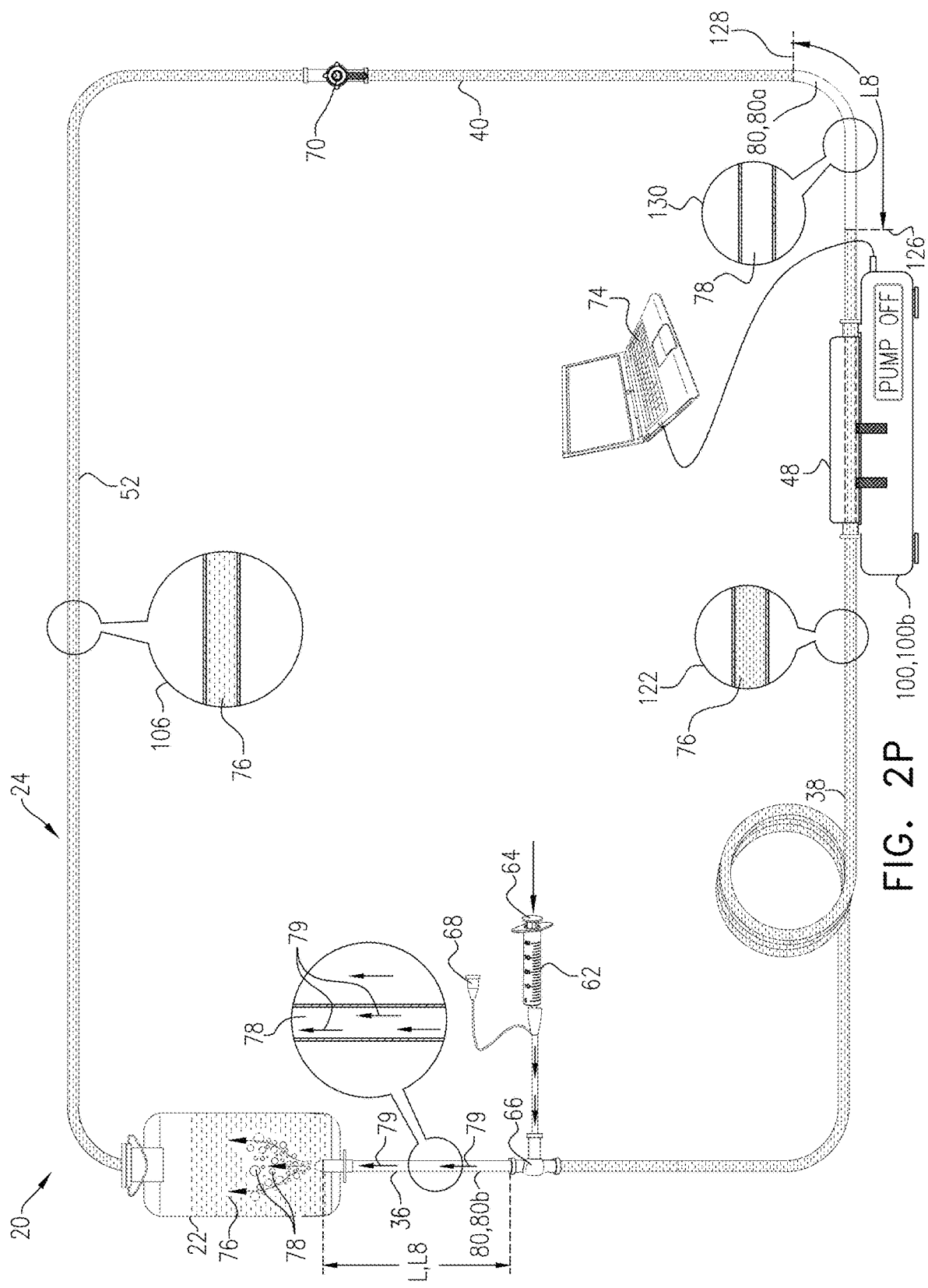
Figure 2Q:
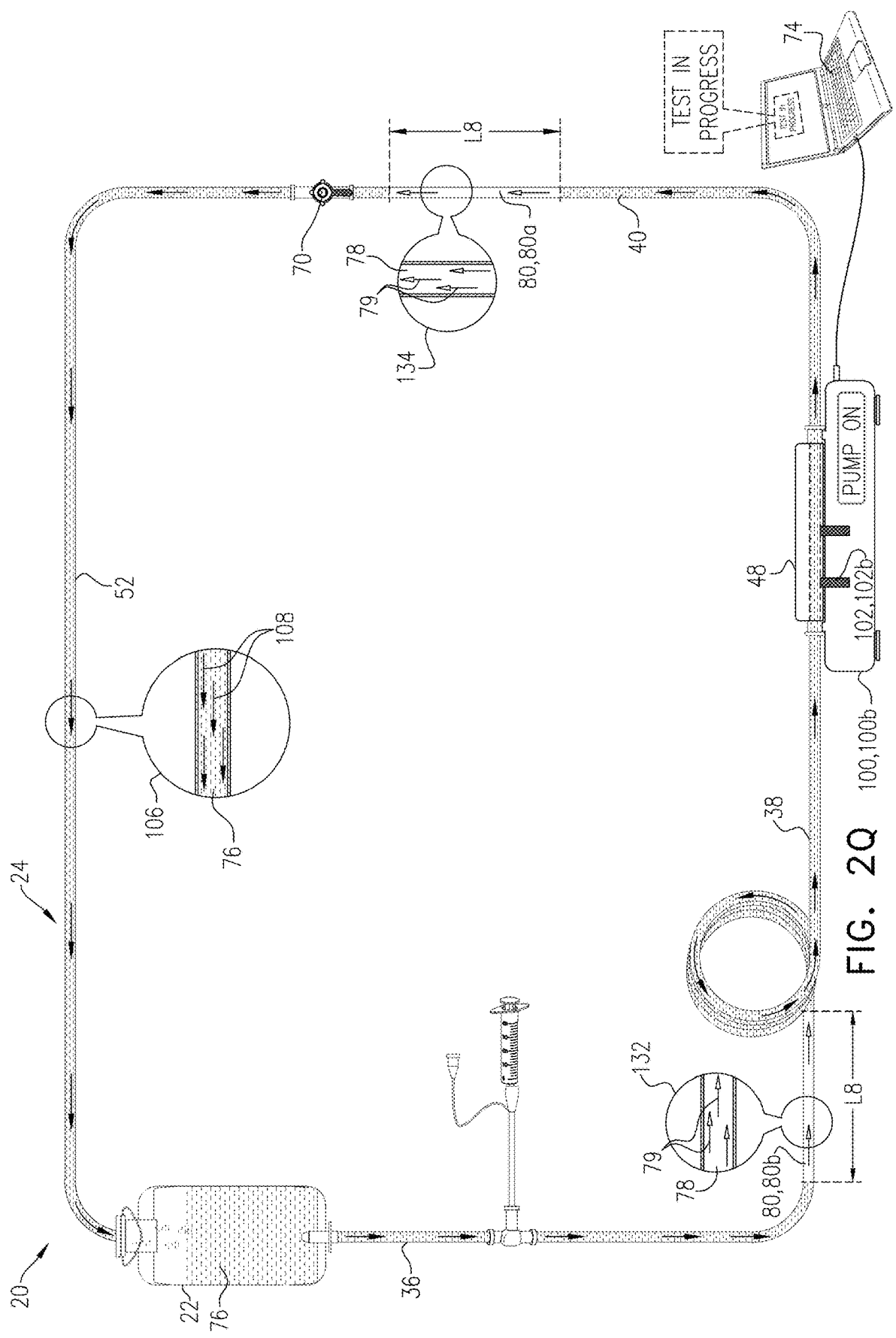
Figure 2R:
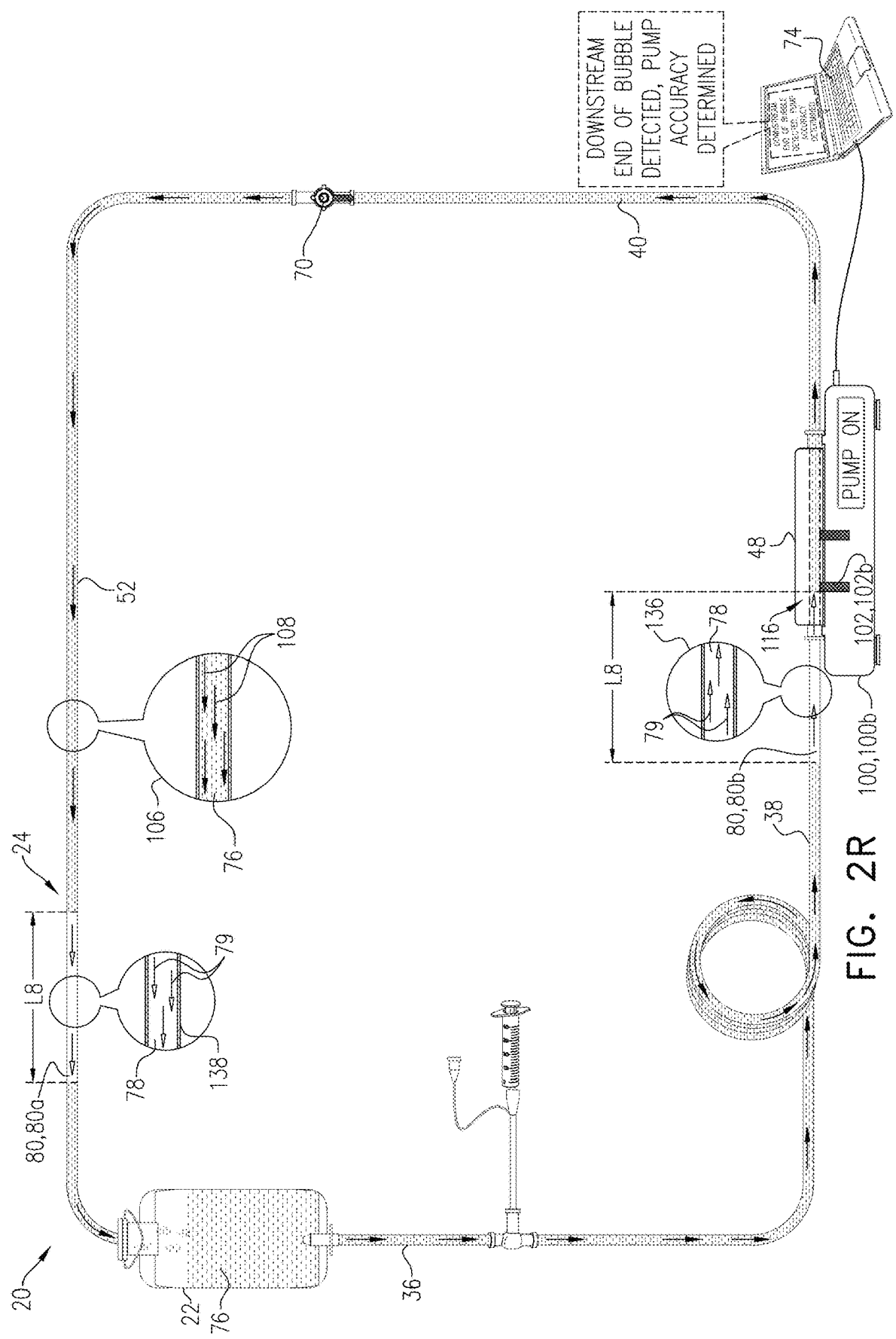
Figure 2S:
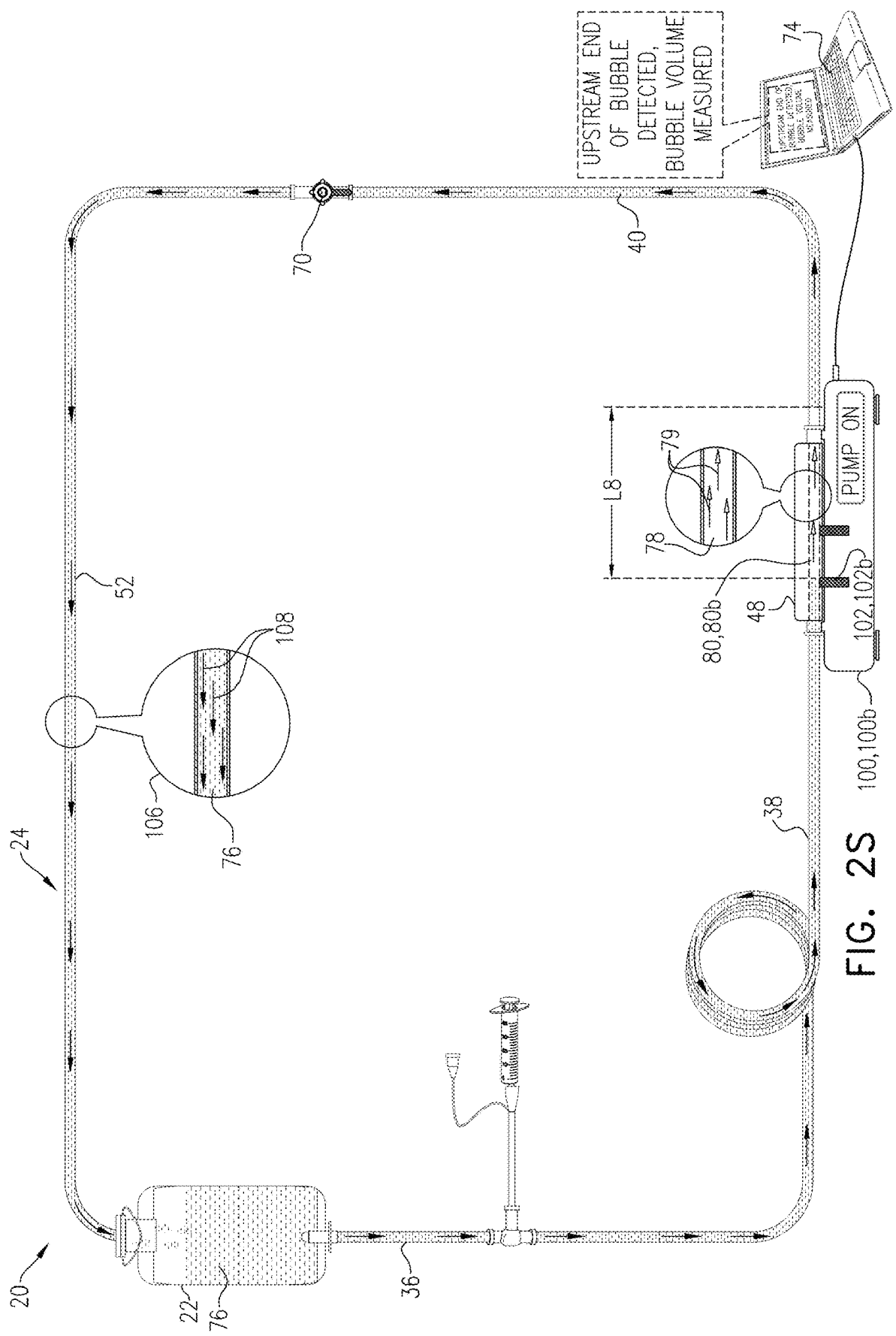
Figure 2T:
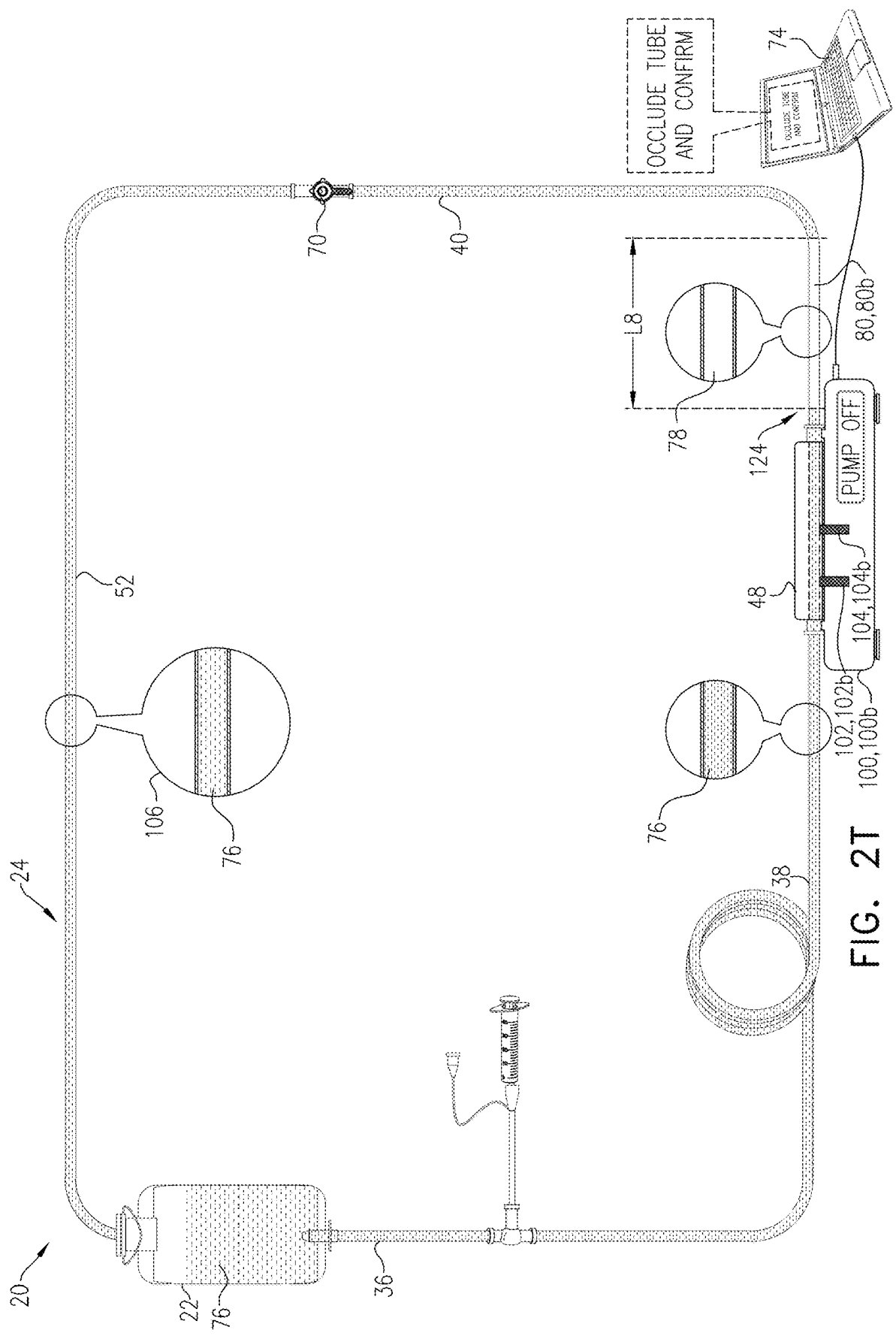
Figure 2V:
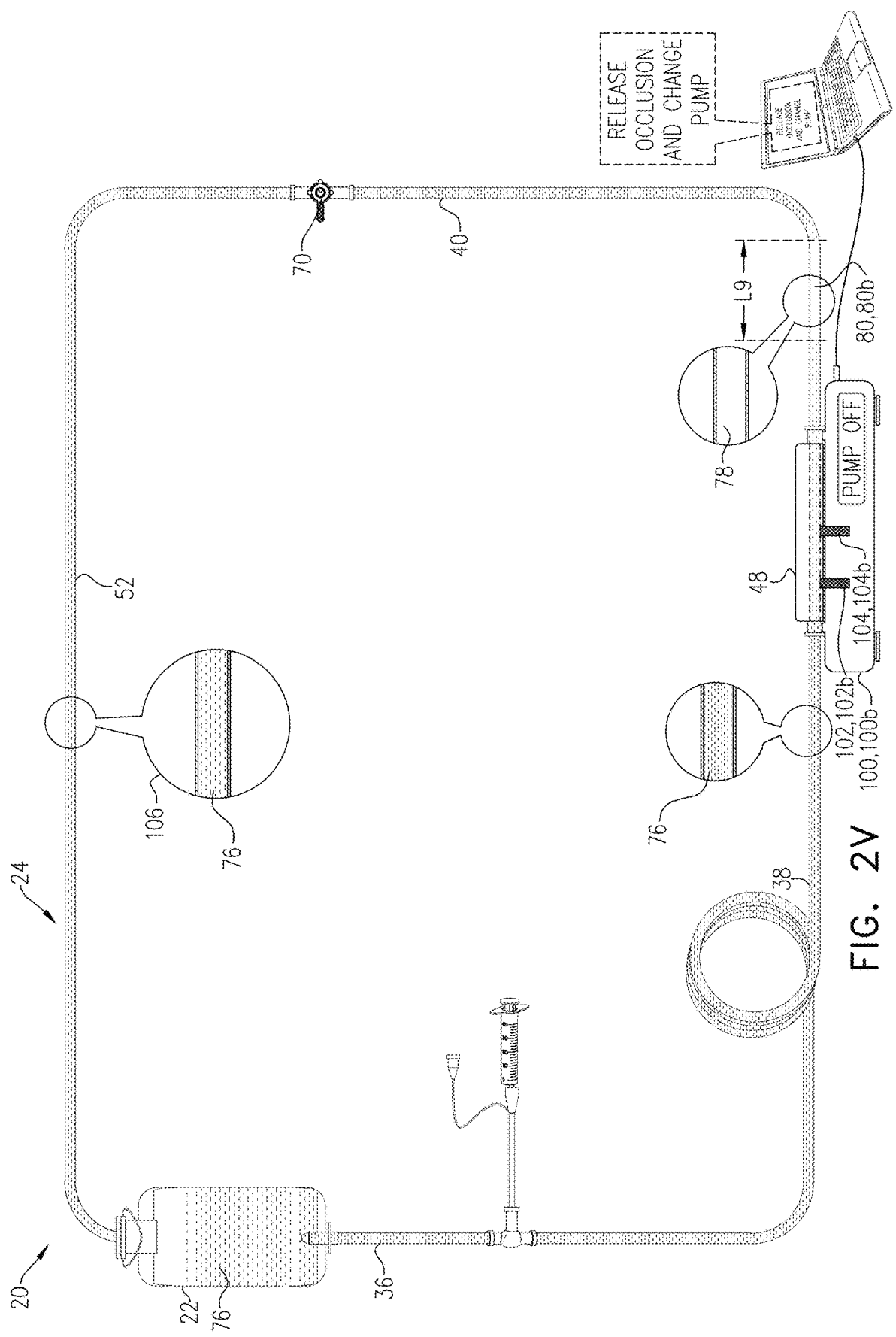
Figure 2W:
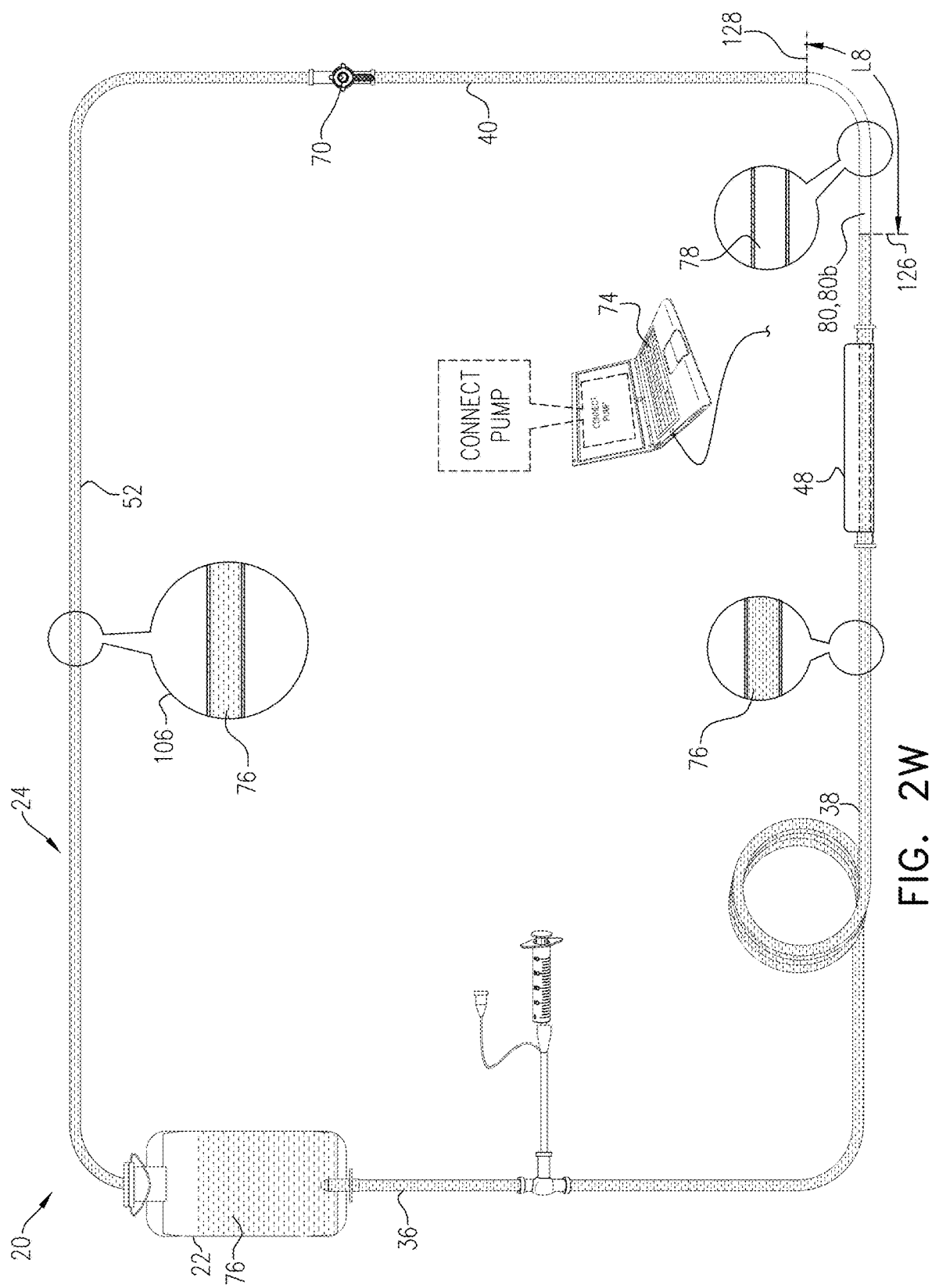

Reference is now made to FIGS. 2A-W, which are schematic illustrations that sequentially illustrate tube set 20 in use, in accordance with some applications of the present invention. FIG. 2A schematically shows tube set 20 after being removed from packaging 25, as it is being arranged for use. An external user interface device 74, e.g., a processor, a computer, or handheld computing device, is typically connected to the pump being tested in order to receive information from the pump, e.g., a serial number unique to a given pump, and/or pump measurements, and to display information, e.g., instructions, and/or analysis of the pump measurements to the user. Reservoir 22 is shown to be filled with liquid 76, e.g., water, and cap 34 is coupled to reservoir 22. As described hereinabove, typically there is a hole in cap 34 of reservoir 22, through which downstream end 28 of tube 24 is disposed, and via which reservoir 22 is open to atmospheric pressure.

Typically, dimensions of the various tube segments (further described hereinbelow) are selected such that (a) second segment 38 defines a predetermined volume of liquid between air port 56 and a pump when tube 24 is filled with liquid, (b) third segment of tube 24 is longer than first segment 36, and (c) third segment 40 of tube 24 is shorter than second segment 38.

As described hereinabove and further described hereinbelow with reference to FIGS. 2E-F, first one-way valve 66 allows air 78 (such as is shown, for example, in FIGS. 2E-F) from within air port 56 to enter first segment 36 of tube 24, i.e., first one-way valve 66 allows an air bubble 80 (such as is shown for example, in FIG. 2F) to be injected into first segment 36. As shown in FIG. 2F, air 78 is inserted into first segment 36 of tube 24 while pump 100 is off and thus blocking any fluid movement in the downstream direction. As a result, as air 78 is inserted into first segment 36 of tube 24, the air can only rise upward toward reservoir 22 such that when first segment 36 is filled with air 78, air bubble spans the length of first segment 36, further described hereinbelow.

In accordance with some applications of the present invention, dimensions of the various segments and components of tube set 20 are as follows, further described hereinbelow:

First segment 36 of tube 24 spans from first one-way valve 66 to reservoir connector 30, and typically has a length L1 of at least 2 cm and/or less than 50 cm, e.g., cm. (Length L1 includes the length of reservoir connector 30.)

Second segment 38 of tube 24 spans from connector 57 to tube cartridge 48, and typically has a length L2 of at least 20 cm and/or less than 200 cm, e.g., 99 cm, as further described hereinbelow. As shown in FIG. 2A, length L2 refers to the length of tube disposed between dashed lines 82 and 84, including the portion of tube 24 that is shown to be coiled, i.e., the length of tubing through which fluid travels from dashed line 82 to dashed line 84.

Connector 57 typically has a length L3 of approximately 1 cm.

Pump segment 50 of tube 24 is typically fixedly disposed within tube cartridge 48 and typically has a length L4 of at least 8 cm and/or less than 16 cm, e.g., 12 cm. Length L4 includes any tube connectors on either side of pump segment 50, for connecting pump segment 50 to second segment 38 and third segment 40.

Third segment 40 of tube 24 spans from tube cartridge 48 to tube-occluding element 70, and typically has a length L5 of at least 20 cm and/or less than 80 cm, e.g., 56 cm. As shown in FIG. 2A length L5 refers to the length of tube disposed between dashed lines 86 and 88, i.e., the length of tubing through which fluid travels from dashed line 86 to dashed line 88.

Tube-occluding element 70 typically has a length L6 of approximately 0.5 cm.

Fourth segment 52 of tube 24 spans from tube-occluding element 70 to downstream end 28 of tube, and typically has a length L7 of at least 10 cm and/or less than 60 cm, e.g., 42 cm. As shown in FIG. 2A, length L7 refers to the length of tube disposed between dashed lines 90 and 92, i.e., the length of tubing through which fluid travels from dashed line 90 to dashed line 92.

The total length of tube set 20 is typically at least 120 cm and/or less than 320 cm, e.g., 224.5 cm.

It is noted that the dimensions of tube set 20 are not shown to scale in FIGS. 2A-W. It is also noted that the dimensions described hereinabove are shown only on FIG. 2A, however they remain the same for tube set 20 as shown in FIGS. 1A-B, and FIGS. 2A-W.

When tube set 20 is assembled, and tube 24 is operatively coupled to a pump air port 56 is typically disposed at a location that is at a height H of at least 0 cm and/or less than 100 cm above the pump, with respect to gravity. Additionally, when tube 24 is operatively coupled to a pump, second segment 38 of tube 24 is maintained between the height of the location above the pump and the pump, with respect to gravity, further described hereinbelow with reference to FIG. 2G. (Thus, height H is defined irrespective of the length of tube in the coiled portion.)

FIGS. 2A-K illustrate sequential steps in a method for performing calibration tests of a pump 100. FIG. 2A shows tube set 20 fully assembled after being removed from commercial packaging 25, and after a user, e.g., a technician performing the tests, has filled reservoir 22 with liquid 76. Typically, user interface device 74 provides the user with step-by-step instructions, e.g., prompts, throughout the testing procedure, including, as further described hereinbelow, letting the user know if an error has occurred and that the test should be repeated. In FIG. 2A, user interface device 74 is shown to be giving an instruction to the user to operatively connect a pump to tube set 20 and to user interface device 74.

FIG. 2B shows a pump 100, e.g., a first pump 100a, operatively coupled to tube 24 via tube cartridge 48. When pump 100 is operatively coupled to tube 24 a bubble detector 102, e.g., an optical bubble detector, and a sensor 104, e.g., a force sensor, are operatively engaged with, e.g., in contact with, pump segment 50 of tube 24. Pump 100 is also connected to user interface device 74, e.g., a processor, a computer, or a handheld computing device. Typically, when the pump is connected to user interface device 74, the pump automatically sends a unique identifier, e.g., a unique serial number, to user interface device 74, such that the results of the calibration tests may be stored for that particular pump, and for some applications, sent to an external server. When user interface device 74 recognizes that pump 100 has been connected and is ready for testing, the user is prompted with instructions to fill tube 24 with liquid 76 from reservoir 22, e.g., to prime tube 24. As further described hereinbelow, this step of priming tube 24 is only performed for first pump 100a. For subsequent pumps connected to the same tube set 20, tube 24 does not have to be primed again.

FIG. 2C shows tube 24 being filled with liquid 76. As seen in the enlarged view circle 106, liquid 76 is now disposed within and moving through tube 24. Typically, pump 100 is used to prime the set by being activated to pump liquid 76 from reservoir 22. Alternatively, for some applications, the user, e.g., technician, may manually fill tube 24 with liquid 76. As shown in FIG. 2C, pump 100 is activated and pumps liquid 76 through tube 24. Enlarged view circle 106 shows liquid 76 now disposed within tube 24 and liquid-flow arrows 108 representing liquid 76 flowing through tube 24.

In accordance with some applications of the present invention, when tube set 20 is filled with liquid 76, the various segments and components of tube set 20 hold the following volumes of liquid:

First segment 36 typically holds at least 0.5 ml and/or less than 3 ml, e.g., 1 ml.

Connector 57 typically holds approximately 0.5 ml.

Second segment 38 of tube 24 typically holds at least 4 ml and/or less than 20 ml, e.g., 7.3 ml.

Pump segment 50, including tube connectors on either side of pump segment 50, typically holds at least 0.5 ml and/or less than 2 ml, e.g., 0.8 ml.

Third segment 40 of tube 24 typically holds at least 2 ml and/or less than 8 ml, e.g., 4 ml.

Fourth segment 52 of tube 24 typically holds at least 1 ml and/or less than 5 ml, e.g., 3 ml.

Full tube set 20 typically holds at least 7 ml and/or less than 30 ml, e.g., 15.9 ml.

Typically, a volume of fluid that is larger than the full volume that tube set 20 can hold, e.g., 2 ml larger, is used in order to prime the set, so as to ensure that indeed the entire tube 24 is filled with liquid 76. Thus, for example, if tube set 20 holds a total of 15.9 ml of liquid, then 17.9 ml of liquid is pumped using pump 100 in order to prime the set. Liquid droplets 110 in FIG. 2C represent the excess fluid returning to reservoir 22 through downstream end 28 of tube 24. The volume of liquid used to prime tube set 20 is predetermined and pump 100 automatically turns off once tube 24 has been primed.

FIG. 2D shows tube set 20 filled with liquid 76. Pump 100 is off, and user interface device 74 is prompting the user to fill syringe 62 with air, inject an air bubble into first segment of tube 24, and confirm the injection of the air bubble, e.g., by pressing a suitable button on user interface device 74. As further described hereinbelow, if the user accidentally confirms the injection of an air bubble without actually injecting an air bubble into tube 24, or before an air bubble of sufficient size has been injected into tube 24, the system identifies this as an error during subsequent testing steps and will prompt the user to insert an air bubble and re-confirm in order to start the test again. Pump 100 remains off until the user confirms that an air bubble has been injected into tube 24.

FIG. 2E shows syringe 62 filled with air 78 after the user has pulled plunger 64. As described hereinabove, due to first one-way valve 66 and second one-way valve 68, when the user pulls plunger 64, only air 78 is allowed to flow into syringe 62. As shown in enlarged view circle 106, tube 24 is filled with liquid, however the liquid is not flowing due to pump 100 being off. Enlarged view circle 112 shows air 78 disposed within syringe 62.

FIG. 2F shows the insertion of air bubble 80, e.g., first air bubble 80a, into first segment 36 of tube 24. As described hereinabove, due to the arrangement of first one-way valve 66 and second one-way valve 68, when the user pushes plunger 64 into syringe 62, air 78 from within syringe 62 is inserted into first segment 36 of tube 24. Typically, syringe 62 holds a larger volume of air than first segment 36 can hold. As air 78 is inserted into tube 24 it rises upwards toward reservoir 22, as illustrated by air-flow arrows 79, such that air bubble 80, e.g., first air bubble 80a, typically fills the entire length of first segment 36, and thus has a length L8 that is typically equal to length L1 of first segment 36. Any air that is inserted into first segment 36 that is in excess of the volume that first segment 36 can hold exits first segment 36 into reservoir 22 through reservoir connector 30 and exit spout 32 of reservoir 22. This allows a user, e.g., the technician, to fully push plunger 64 into syringe 62 without having to be careful to input a correct amount of air. Since reservoir 22 is open to the atmosphere, position while air bubble 80 is being inserted, the insertion of air bubble 80 into tube 24 does not increase pressure within tube 24. Due to the dimensions of tube set 20 described hereinabove, once air bubble 80 has been inserted into tube 24 there is a predetermined, known, volume of liquid 76 between air bubble 80, i.e., a downstream end 116 of air bubble 80, and pump 100. For example, the predetermined volume of liquid may be 0.1 ml of liquid 76 within connector 57 plus 7.3 ml of liquid 76 in second segment 38.

FIG. 2G shows the test in progress after the user has confirmed the insertion of air bubble 80. Pump 100 is used to advance air bubble 80 along tube 24, i.e., along second segment 38 of tube 24, to bubble detector 102 of pump 100. Enlarged view circle 106 again shows liquid 76 flowing through tube 24, and enlarged view circle 118 shows air 78 within air bubble 80 that is now advancing through second segment 38. Using pump 100 to advance air bubble 80 along tube 24 typically drives liquid 76 within tube 24 that is downstream of pump 100 to advance along tube 24 and subsequently exit tube 24 into reservoir 22, as illustrated by liquid droplets 110 in FIG. 2G. As air bubble 80 is being advanced to bubble detector 102, pump 100 is used to measure, e.g., the pump automatically measures, the volume of liquid 76 that is pumped in order to advance air bubble 80 to bubble detector 102.

For some applications, pump 100 measures the volume of liquid 76 that is pumped to advance air bubble 80 to bubble detector 102 by assessing, e.g., counting, the number of pumping cycles during which pump 100 advances air bubble 80 to bubble detector 102. Pump 100 may assess, e.g., count, an integer number of pumping cycles of pump 100 as well as a non-integer number of pumping cycles of pump 100. It is possible that when downstream end 116 of air bubble 80 reaches bubble detector 102, pump 100 may be in the middle of a pumping cycle. Thus, in order for pump 100 to measure the volume pumped it must know exactly where in the current pumping cycle bubble detector 102 detected downstream end 116 of air bubble 80. Typically, a DC motor that comprises an indexed encoder is used to run pump 100. When bubble detector 102 detects downstream end 116 of air bubble 80, exactly which encoder the DC motor is at indicates to pump 100 where in the pumping cycle pump 100 is, which indicates the volume pumped up to that point in the pumping cycle.

Based on the volume of liquid 76 that is pumped to advance air bubble 80 to bubble detector 102, as measured by pump 100, a parameter, e.g., accuracy of pump 100, e.g., a level of pumping accuracy of pump 100, is determined. Typically, the pumping accuracy is determined by a comparison between (i) the measured volume of liquid 76 pumped, e.g., as determined by the number of pump cycles counted by pump 100, and (ii) the predetermined volume of liquid 76 between downstream end 116 of air bubble 80 and pump 100, as defined by the dimensions of tube set 20 described hereinabove. For some applications, determining the accuracy of pump 100 includes determining a volume of liquid 76 that is pumped per pumping cycle of pump 100. In order for pump 100 to accurately maintain set flow rates while in operation, e.g., while delivering a therapeutic or diagnostic substance to a subject, it is important that the volume of liquid being pumped per pumping cycle be properly calibrated.

As described hereinabove, as air bubble 80 is advanced to bubble detector 102 of pump 100, air bubble 80 advances along a length of tube that is at least 20 cm and/or less than 200 cm, e.g., 99 cm, long. The inventor has realized that if second segment 38 is too short, the results of the pumping accuracy determination may not be accurate. Thus, it is important for second segment 38 of tube 24 to be long enough in order for the results of the pumping accuracy determination to be accurate.

The inventor has also realized that, due to the tendency of air to float in liquid, if tube 24 is positioned such that large portions of second segment 38 are vertical with respect to gravity, air bubble 80 may tend to float upwards while pump 100 is trying to advance it toward bubble detector 102. Thus, when assembled, air port 56 and pump 100 are positioned such that pump 100 advances air bubble 80 from a location that is at height H above pump 100 with respect to the direction of gravity. Height H is at least 0 cm and/or less than 100 cm. Furthermore, the inventor has realized that it is advantages to ensure that the entire length of tube in second segment 38 is maintained between the height of air port 56 and pump 100 with respect to the direction of gravity, such that air bubble 80 is maintained between the height of air port 56 and pump 100 as air bubble 80 advances through second segment 38. Since second segment 38 is typically relatively long, e.g., 99 cm, a portion 120 of second segment is typically coiled up, such that the entire length of second segment 38 is situated between air port 56 and pump 100 with respect to the direction of gravity.

FIG. 2H shows downstream end 116 of air bubble 80 having reached bubble detector 102. For some applications, user interface device 74 may display an indication to the user that downstream end 116 of air bubble 80 has been detected and the pump accuracy determined, as described hereinabove. As shown in enlarged view circles 106 and 122, liquid 76 is still advancing through tube 24, and pump 100 is on, i.e., after pump 100 advances air bubble 80 to bubble detector 102, pump 100 continues to advance air bubble 80 along tube 24 without stopping, such that air bubble 80 advances past bubble detector 102, e.g., past pump 100, such as is shown in FIG. 2I.

FIG. 2I shows air bubble 80 after having advanced past bubble detector 102 of pump 100. Pump 100, e.g., bubble detector 102 of pump 100, is used to measure the volume V0 of air bubble 80 as air bubble 80 is advanced past bubble detector 102. Typically, pump 100 measures volume V0 of air bubble 80 by assessing, e.g., counting, the number of pumping cycles of pump 100 during the advancing of air bubble 80 past bubble detector 102 of pump 100. As described hereinabove, pump 100 typically assesses the number of full and partial pumping cycles, e.g., using an indexed encoder as described above, to determine an exact volume of air bubble 80. (For example, pump 100 may measure the air 14 times during one pump cycle, which may create an inaccuracy of up to +/−2.5 microliters in the volume of the air bubble 80. This is considered by the inventor to be a small and insignificant level of error.) Liquid-flow arrows 108 in enlarged view circles 106 and 128 show that pump 100 continues running after volume V0 of air bubble 80 is measured, in order to advance air bubble 80 fully past pump 100. If the user made an error when inserting air bubble 80 into tube 24 such that air bubble 80 is too small, e.g., less than 0.5 ml, after air bubble 80 is measured pump 100 will stop and the user will be asked to insert another air bubble and confirm in order to start the test again for that pump.

FIG. 2J shows air bubble 80 after having advanced past pump 100. At this point in the test, pump 100 has been on and pumping since the user confirmed the insertion of air bubble 80. Typically, pump 100 automatically stops after pumping a predetermined volume of liquid 76 so as to ensure that the entire air bubble 80 has passed pump segment 50 of tube 24 and is disposed within third segment 40, i.e., upstream end 124 of air bubble 80 is downstream of pump 100 and downstream end 116 of air bubble is upstream of tube-occluding element 70. For example, using numbers from within the ranges provided hereinabove, pump 100 may pump a volume equal to 0.1 ml in connector 57+7.3 ml in second segment 38, 0.8 ml in pump segment 50+an extra delta of liquid 76, e.g., 1 ml, that ensures an upstream end 124 of air bubble 80 is downstream of pump segment 50, such as is shown in FIG. 2J. No liquid-flow arrows are shown in enlarged view circles 106 and 122, due to pump 100 being off.

As described hereinabove, it is important that third segment 40 be longer than first segment 36 so as to ensure that the entirety of air bubble 80 is disposed within third segment 40 at this point in the test. Furthermore, it is possible that as air bubble 80 advances through tube 24, the air bubble will split into a plurality of smaller air bubbles that may be spaced apart from each other by small volumes of liquid 76. Thus, by the time air bubble 80 is past pump 100, the length of tube between downstream end 116 of air bubble 80 and upstream end 124 of air bubble 80 may be longer than length L1 of first segment 36 (where the air bubble was originally inserted). Thus, typically, length L5 of third segment 40 (shown in FIG. 2A) is at least 20% and/or less than 50% longer than length L1 of first segment 36 (shown in FIG. 2A) of first segment 36.

With regards to potential user errors, the system as described hereinabove is generally immune to user errors having to do with insertion of air bubble 80. If the user inserts too much air, the excess air simply exits tube 24 into reservoir 22 without any effect on the length of the air bubble, as described hereinabove. If the user, in error, forgot to insert air bubble 80 but confirmed the insertion of air bubble 80, pump 100 will start to run as if to perform the first stage of the test, i.e., pumping accuracy determination. After pumping a predetermined volume of liquid 76 that is large enough such that downstream end 116 of air bubble 80 should have been detected by bubble detector 102, pump 100 will stop and alert the user than an error has occurred. The user will be given instructions to insert an air bubble and confirm in order to restart the test. If the user inserts air bubble 80, but does not insert enough air, e.g., less than 0.5 ml, then when pump 100 measures volume V0 of air bubble 80, pump 100 will stop and alert the user than an error has occurred. The user will be given instructions to insert another air bubble and confirm in order to restart the test.

After the upstream end of air bubble 80 is downstream of pump 100, the user is given instructions to occlude tube 24 downstream of air bubble 80 with tube-occluding element 70, and to confirm the occlusion in order to move on to the calibration test of an occlusion sensor, e.g., force sensor 104 of pump 100.

FIG. 2K shows pump 100 being used to increase pressure within tube 24 by pumping a volume of liquid 76 while tube 24 is occluded. Liquid 76 between downstream end 116 of air bubble 80 and tube-occluding element 70 is not compressible, however air 78 within air bubble 80 is compressible. As pump 100 pumps the volume of liquid, air bubble 80 is compressed by the volume of liquid pumped (Vp), thereby increasing pressure within tube 24. Compressed air bubble 80 has a length L9 that is shorter than original length L8 of air bubble 80. Typically, pump 100 pumps liquid 76 until pump 100 measures a preset pressure or more than one pressure stopping points are set and pump 100 measures each one of the preset pressure values (e.g., 0.4 bar, 0.8 bar, or 1.2 bar), at which point pump 100 stops. The volume pumped (Vp) is used together with the measured air bubble volume V0 to calculate the expected pressure Pexp (P1 in the equation below) upon compression of the air bubble. The expected pressure is then compared with the measured pressure value. The calculation of the expected pressure is based on Boyle's law P0*V0=P1*V1, where:

(i) P0 is typically atmospheric pressure prior to air bubble 80 being compressed, (ii) V0 is the measured volume of air bubble 80 prior to being compressed, (iii) V1 is the compressed volume of air bubble 80, which is calculated based on the volume pumped (Vp) and the measured volume V0, and (iv) P1 is the calculated expected pressure when air bubble 80 is compressed. For example, if Vp=0.5*V0 then the expected pressure increase is 1 bar. If Vp=⅓*V0, then the expected pressure increase is 0.5 bar.

The occlusion sensor, e.g., force sensor, 104 then measures the increase dP (measured) in pressure within tube 24. The calculated (expected) and measured pressures are compared, and if the difference between them is within the tolerances of pump 100 then the test of the pressure sensor is considered to indicate proper functioning of pump 100, and if not, a malfunction of pump 100. For some applications, pump 100 pumps liquid 76 until pump 100 measures a volume pumped (Vp) that is equal to another value that is a percentage, e.g., 20%-60%, of volume V0 of air bubble 80. To avoid excess pressure, a maximum Vp (Vpmax) is typically set such that the pump stops if Vp>Vpmax, even if the expected pressure was not reached. This could potentially happen in a case where there are errors in V0 or dP measurements.

Based on the measured volume V0, the measured volume of liquid 76 pumped in order to compress air bubble 80, and the fact that before tube 24 was occluded liquid 76 within tube 24 was exposed to atmospheric pressure P0 of typically 1 bar, the following equation may be used to assess, e.g., calculate an expected increase in pressure dP(expected):

$$[P0+dP(expected)]*V1=P0*V0 \quad [\text{Eqn 1}]$$

which translates to (as an example):

$$dP(expected)=V0*[1/(V0-V0/3)]-1=1.5-1=0.5 \text{ bar}$$

Thus, the expected increase in pressure of typically 0.5 bar is compared to the sensed increase in pressure dP (measured), as measured by occlusion sensor, e.g., force sensor, 104 in response to pump 100 pumping volume Vp, in order to assess the accuracy of occlusion sensor, e.g., force sensor, 104. As described hereinabove, if air bubble 80 is measured to be too small, e.g., less than 0.5 ml, then the user is asked to restart the test. This is due to the inventor having realized that if air bubble 80 is too small, the results of the force sensor accuracy determination may not be accurate.

Liquid-flow arrows 108, as shown in enlarged view circle 122, illustrate that when pump 100 is on after tube 24 has been occluded, liquid 76 flows toward air bubble 80, but there is no liquid flow downstream of air bubble 80 (due to the incompressible nature of the liquid). Thus, no liquid-flow arrows appear in third segment 40 downstream of air bubble 80, and no liquid-flow arrows appear in fourth segment 52.

After pump 100 measures the sensed increase in pressure dP (measured) and compares it with the expected, calculated, increase in pressure, e.g., 0.4 bar, pump 100 continues to pump liquid 76 until a sensed pressure of at least 1.0 bar and/or less than 1.6 bar, e.g., 1.2 bar, is sensed. This verifies that pump 100 can generate a pressure equal to a maximum occlusion setting, and can detect it. The user is then prompted with instructions to remove the occlusion of tube 24, e.g., to turn occlusion element 70 to an open position, or to remove a sliding clamp from tube 24, and to change the pump that is operatively coupled to tube set 20 and user interface device 74, such as is shown in FIG. 2L.

FIG. 2M shows tube set 20 after the occlusion of tube 24 has been released and first pump 100a is no longer coupled to tube set 20 and user interface device 74. When the occlusion of tube 24 is released, air bubble 80, i.e., first air bubble 80a, will expand to its original volume. During the expansion of air bubble 80 back to its original volume, liquid 76 downstream of air bubble 80 is pushed along tube 24 such that some liquid 76 from within fourth segment 52 enters reservoir 22. In FIG. 2M, air bubble 80 is disposed between dashed lines 126 and 128, and labeled with L8, indicating that air bubble 80 has expanded back to its original volume.

FIG. 2N shows a second pump 100b operatively coupled to tube 24 via tube cartridge 48 and to user interface device 74. As described hereinabove, when second pump 100b is connected to user interface device 74, second pump 100b sends a unique identifier, e.g., a unique serial number, to user interface device 74 such that the results of the calibration tests may be stored for second pump 100b. Once user interface device 74 recognizes that second pump 100b has been connected, the user is once again prompted with instructions to fill syringe 62 with air 78, inject a second air bubble 80b into first segment of tube 24, and confirm the injection of the air bubble. As illustrated by FIGS. 2N-W, the same testing procedure that was performed for first pump 100a is performed for second pump 100b, and for subsequent pumps following second pump 100b. Typically, the same tube set 20, i.e., the same tube 24, may be used to test at least 10 and/or less than 50 pumps, e.g., 30 pumps, before tube 24 may start to degrade and affect the accuracy of the test results. Typically, a plurality of pumps are tested, e.g., as a batch, and then the pumps that are determined to be in good working order are put back in use, while any pumps that are determined to not be in good working order may be sent for repair, e.g., back to the manufacturer. Thus, after a pump is finished being tested, the next pump is coupled to tube set 20 to be tested, without the first pump being used to administer anything to a patient prior to the next pump being tested.

FIG. 2O shows syringe 62 again filled with air 78 after the user has pulled plunger 64. It is noted that first air bubble 80a is still disposed within third segment 40, as illustrated by enlarged view circle showing air 78 of first air bubble 80, which is disposed between dashed lines 126 and 128. Typically, the testing steps are repeated for pump 100b without the user, e.g., technician, having to prime tube set 20 again. That is, after tube set 20 is primed, i.e., filled with liquid for the testing of first pump 100a, tube set 20 does not have to be primed again. After testing 10-50 pumps, as described hereinabove, the technician typically uses a second tube set 20, and primes second tube set 20 prior to testing a first pump 100a for that tube set.

FIG. 2P shows the insertion of second air bubble 80b into first segment 36 of tube 24. Due to reservoir 22 being open to the atmosphere, the insertion of second air bubble 80a is also without increasing pressure within tube 24, and additionally does not cause any movement in liquid 76 that is disposed downstream of air port 56, as illustrated by lack of liquid-flow arrows in tube 24. Air-flow arrows 79 in first segment 36 illustrate air 78 rising toward reservoir 22 as second air bubble 80b fills first segment 36.

FIG. 2Q shows the test in progress after the user has confirmed the insertion of second air bubble 80b. As second pump 100b is used to advance second air bubble 80b to bubble detector 102b of second pump 100b, first air bubble 80a advances along tube 24 as well. Enlarged view circle 132 shows air 78 of second air bubble 80b as it advances through second segment 38, and enlarged view circle 134 shows air 78 of first air bubble 80a as it simultaneously advances along third segment 40. The respective volumes of both air bubbles are approximately the same at this point in the process.

FIG. 2R shows downstream end 116 of second air bubble 80b having reached bubble detector 102b of second pump 100b, such that a parameter, e.g., accuracy, e.g., level of pumping accuracy, of second pump 100b is determined, as described hereinabove with reference to the first pump. As described hereinabove, third segment 40 is shorter than second segment 38, such that as the volume of liquid held in second segment 38 is pumped in order to advance second air bubble 80b to bubble detector 102b of second pump 100b, first air bubble 80a advances by the same volume, and thus necessarily will be disposed downstream of tube-occluding element 70, within fourth segment 52, by the time downstream end 116 of second air bubble 80b is detected by bubble detector 102. Typically, length L2 (shown in FIG. 2A) of second segment 38 is at least 20% and/or less than 80% longer than length L5 (shown in FIG. 2A) of third segment 40. In FIG. 2R, first air bubble 80a is shown disposed within fourth segment 52, as illustrated by air 78 shown in enlarged view circle 138 and length L8 of first air bubble 80a. As second pump 100b continues to run for the rest of the testing of second pump 100b, first air bubble 80a typically exits tube 24 into reservoir 22.

FIG. 2S shows second air bubble 80b having advanced past bubble detector 102b of second pump 100b. At this point, first air bubble 80b may have exited tube 24 into reservoir 22, and as such first air bubble 80a is not shown within tube 24 in FIG. 2S. For some applications, first air bubble 80a may still be disposed within fourth segment 52, however since first air bubble 80a is necessarily entirely downstream of tube-occluding element 70, its presence within tube 24 is irrelevant to calibration tests being performed on second pump 100b. The volume V0 of second air bubble 80b is measured and the occlusion sensor, e.g., force sensor, 104b test is carried out for second pump 100b, as described hereinabove with reference to the first pump.

FIG. 2T shows second air bubble 80b disposed within third segment 40, and the user receives instructions to occlude tube 24 and confirm. FIG. 2U shows second air bubble 80a being compressed as second pump 100b is used to increase pressure within tube 24 in order to test the accuracy of occlusion sensor, e.g., force sensor, 104b of second pump 100b, as described hereinabove with reference to the first pump. FIG. 2V shows tube set 20 after the test of second pump 100b are complete, and the user again receives instructions to remove the occlusion of tube 24 and connect a next pump. FIG. 2W shows tube set 20 ready for the next pump to be connected.

Figure 3:
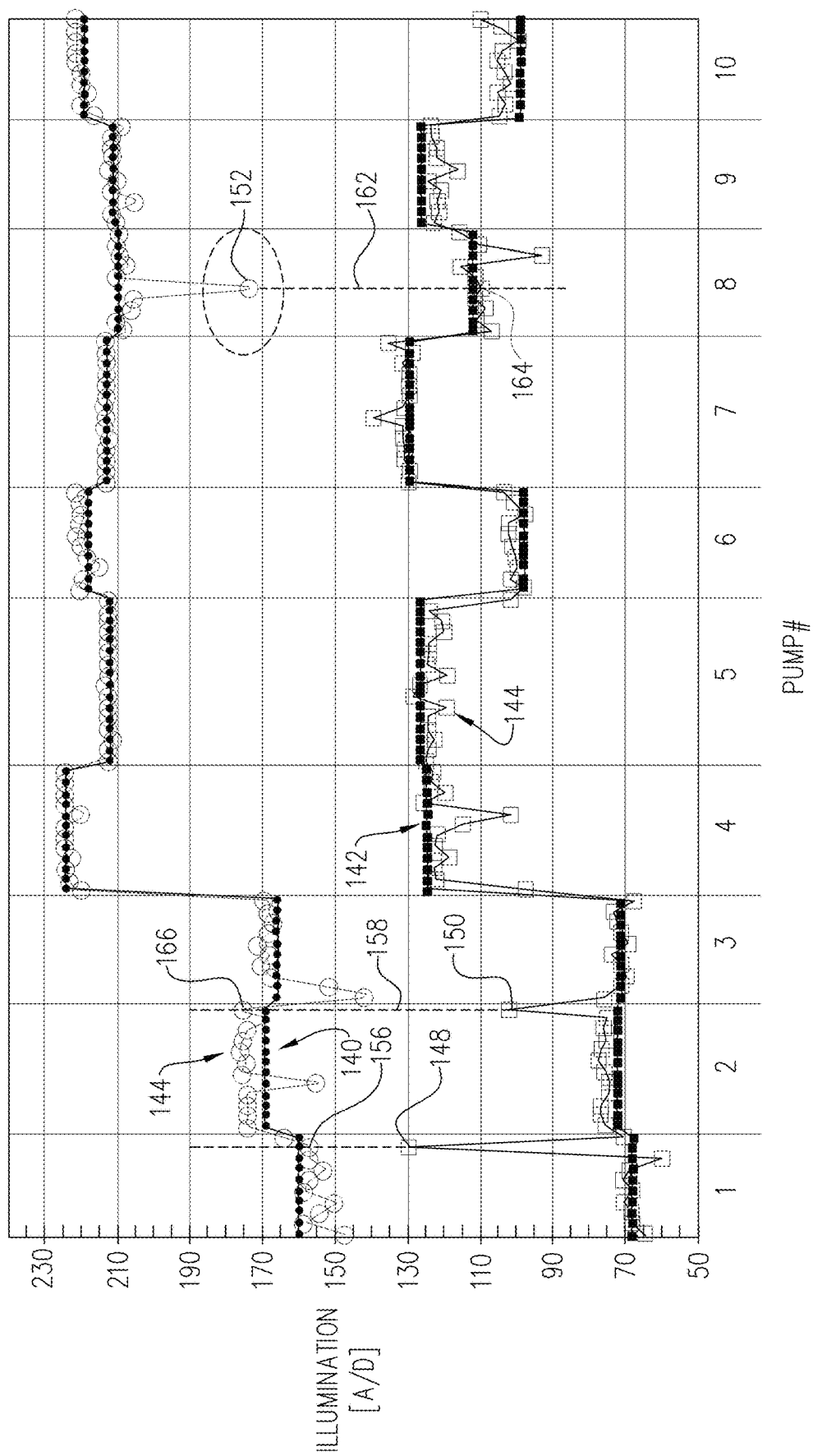
FIG. 3 is a graph showing experimental results for ten bubble detectors of a respective ten pumps, in accordance with some applications of the present invention.

Reference is now made to FIG. 3, which is a graph showing experimental results for ten bubble detectors 102 of a respective ten pumps 100, in accordance with some applications of the present invention. For any given pump 100, bubble detector 102 has (a) a pump-specific liquid-signal, e.g., an analog-to-digital (A/D) signal of a specific value, when that bubble detector detects liquid, and (b) a pump-specific air signal, e.g., an A/D signal of a specific value, when that bubble detector detects air. In FIG. 3, the values of the respective pump-specific liquid signal for each of the ten pumps tested are represented by the small solid circles 140. The values of the pump-specific air signals for each of the ten pumps tested are represented by the small solid squares 142.

If the bubble detector 102 of a pump 100 is in good working condition, e.g., is properly calibrated, then, while the pump 100 is in use, (a) the values of the liquid-signals, e.g., A/D liquid-signals, generated by the bubble detector 102 when liquid is passing the bubble detector 102 should typically fall within a predetermined range of values that is typically within a delta of +/−30 from the value of the pump-specific liquid-signal for that pump 100, and (b) the values of the air-signals, e.g., A/D air-signals, generated by the bubble detector 102 when air is passing the bubble detector 102 should typically fall within a predetermined range of values that is typically within a delta of +/−20 from the pump-specific air signal for that pump 100. The larger empty circles 144 in FIG. 3 represent measured values of respective liquid-signals, e.g., A/D liquid signals, generated in response to each of the 10 bubble detectors detecting liquid 76 within tube 24. The larger empty squares 146 represent measured values of respective air-signals, e.g., A/D air-signals, generated in response to each of the ten bubble detectors detecting air 78 within tube 24. A plurality of experiments were performed for each of the ten pumps. For each experiment there is shown a corresponding larger empty circle 144 and larger empty square 146, representing the measured values of the respective A/D liquid-signal and A/D air signal measure for that particular experiment with that pump.

The inventor has realized that it is highly unlikely for a bubble detector 102 that is not in working order, e.g., not properly calibrated, to "accidentally" generate a signal that is within the expected predetermined range. Thus, for example, as illustrated by data point 152 in FIG. 3, if a given bubble detector 102 generates a liquid-signal having a value that is within the respective predetermined range, but generates an air-signal having a value that is not within the respective predetermined range, it can still be assumed that the bubble detector is in working order, and that likely an unrelated circumstance caused the air-signal to be out of range. The same is true vice versa, for example, as illustrated by data points 148 and 150 in FIG. 3, i.e., if a given bubble detector generates an air-signal having a value that is within range, but a liquid-signal that is out of range, it can still be assumed that the bubble detector is in working order.

Data point 148 represents the value of an A/D air-signal for one of the experiments performed using the pump #1 in the experiment. As shown, data point 148 is out of range, i.e., the difference between (a) the A/D air-signal measured for data point 148 and (b) the pump-specific A/D air-signal for the pump #1, is greater than a chosen delta (e.g., a delta of 20). However, as illustrated by dashed line 154, the corresponding data point 156, representing the A/D liquid-signal measured in the same experiment with pump #1 is within range, i.e., the difference between (a) the A/D liquid-signal measured for data point 156 and (b) the pump-specific A/D liquid-signal for the pump #1, is less than a chosen delta (e.g., a delta of 30). The inventor's realization that the above described pattern can be assumed to indicate a properly-working bubble detector is supported by the remaining data points representing values of the respective A/D liquid-signals and A/D air-signals for other experiments run with pump #1. It is apparent that the bubble detector of pump #1 is in proper working order.

Similarly, data point 150, representing the value of an A/D air-signal measured during an experiment with pump #2, is out of range, i.e., the difference between (a) the A/D air-signal measured for data point 150 and (b) the pump-specific A/D air-signal for the pump #2, is greater than a chosen delta (e.g., a delta of 20). However, as illustrated by dashed line 158, the corresponding data point 160, representing the value of an A/D liquid-signal measured during the same experiment with pump #2, is within range, i.e., the difference between (a) the A/D liquid-signal measured for data point 160 and (b) the pump-specific A/D liquid-signal for the pump #2, is less than a chosen delta (e.g., a delta of 30). Once again, the remaining data points from the other experiments performed with pump #2 confirm that pump #2 is in proper working order.

Similarly, data point 152, representing the value of an A/D liquid-signal measured during an experiment with pump #8, is out of range, i.e., the difference between (a) the A/D liquid-signal measured for data point 152 and (b) the pump-specific A/D liquid-signal for the pump #8, is greater than a chosen delta (e.g., a delta of 30). However, as illustrated by dashed line 162, the corresponding data point 164, representing the A/D air-signal measured in the same experiment with pump #8, is within range, i.e., the difference between (a) the A/D air-signal measured for data point 164 and (b) the pump-specific A/D air-signal for the pump #8, is less than a chosen delta (e.g., a delta of 20). Once again, the remaining data points from the other experiments performed with pump #8 confirm that pump #8 is in proper working order.

Thus, during the calibration testing procedure described hereinabove, a parameter of bubble detector 102 may be determined by measuring respective values of (a) the liquid-signals generated by bubble detector 102 as liquid 76 is passing bubble detector 102 and (b) the air-signals generated by bubble detector 102 when air bubble 80 is passing bubble detector 102. If at least one of the two signals, i.e., if the generated liquid-signal or the generated air-signal, is within the respective predetermined range of values, then a determination may be made that bubble detector 102 is in working order, e.g., is properly calibrated. For example, bubble detector 102 may be determined to be in working order already before air bubble 80 is detected by bubble detector 102 if the values of the generated liquid-signals, e.g., A/D liquid-signals generated by bubble detector 102 in response to liquid 76 advancing past bubble detector 102 are within the respective predetermined range.

Alternatively, if the values of the generated liquid-signals, e.g., A/D liquid-signals, are not within the predetermined range, then a determination may be made after measuring the value of the air signals, e.g., generated in response to bubble detector 102 detecting air bubble 80. If the generated air-signal, e.g., A/D air signal, is within the respective predetermined range, then bubble detector 102 is considered to be in good working order. If the values of both the generated liquid-signal, e.g., A/D liquid-signal, and the generated air-signal, e.g., A/D air-signal, are not within their respective predetermined ranges, then bubble detector 102 is determined to not be working properly, and the test is stopped. Typically, the user will be instructed at that point to remove the pump and start testing the next pump.

Similarly with the pumping accuracy test and occlusion sensor tests, if at any point a pump 100 or a component, e.g., sensor, of pump 100 is determined to not be in working order, the test is immediately stopped and the user asked to move on to the next pump. Typically, the entire test of first pump 100a takes approximately a minute and a half, and the entire test of subsequent pumps (for which tube set 20 does not have to be primed) takes about approximately a minute.

Applications of the invention described herein can take the form of a computer program product accessible from a computer-usable or computer-readable medium (e.g., a non-transitory computer-readable medium) providing program code for use by or in connection with a computer or any instruction execution system, such as user interface device 74. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semi-conductor or solid-state memory, a random-access memory (RAM), a read-only memory (ROM). For some applications, cloud storage, and/or storage in a remote server is used.

A data processing system suitable for storing and/or executing program code will include at least one processor (e.g., a processor of user interface device 74) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of some applications of the present invention may be written in any combination of one or more programming languages, including an object-oriented programming language such as Java, Smalltalk, C++ or the like and conventional procedural programming languages, such as the C programming language or similar programming languages.

It will be understood that the methods described herein can be implemented by computer program instructions. These computer program instructions may be provided to a processor of a general-purpose computer, special purpose computer, or other programmable data processing apparatus to produce a machine, such that the instructions, which execute via the processor of the computer (e.g., user interface device 74) or other programmable data processing apparatus, create means for implementing the functions/acts specified in the methods described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the methods described in the present application. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the methods described in the present application.

User interface device 74 is typically a hardware device programmed with computer program instructions to produce a special purpose computer. For example, when programmed to perform the methods described herein, the computer processor typically acts as a special purpose computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a pump, the method comprising:
   (A) placing liquid in a tube that is coupled to the pump;
   (B) creating an air bubble in the tube by injecting air into the tube (a) in a manner that does not increase pressure within the tube, and (b) such that there is a predetermined volume of liquid between the air bubble and the pump;
   (C) using the pump to advance the air bubble along the tube to the bubble detector of the pump;
   (D) using the pump, assessing accuracy of the pump by automatically measuring the volume of liquid pumped to advance the air bubble to the bubble detector;
   (E) using the pump to continue advancing the air bubble along the tube, past the bubble detector, and using the pump to measure a volume of the air bubble;
   (F) subsequently, occluding the tube downstream of the air bubble;
   (G) using the pump to increase pressure within the tube by pumping a volume of liquid;
   (H) using the pump to measure the volume of liquid pumped to increase pressure within the tube;
   (I) assessing the increase in pressure within the tube based on (a) the measured volume of liquid pumped to increase the pressure within the tube and (b) the measured volume of the air bubble;
   (J) using a sensor of the pump, measuring a sensed increase in pressure in the tube in response to the pumping of the volume of liquid; and
   (K) assessing accuracy of the sensor based on the assessed increase in pressure and the sensed increase in pressure.

2. The method according to claim 1, wherein automatically measuring the volume of liquid pumped to advance the air bubble to the bubble detector comprises automatically assessing the number of pumping cycles during which the pump advances the air bubble to the bubble detector.

3. The method according to claim 1, wherein assessing accuracy of the pump comprises determining a volume of the liquid that is pumped per pumping cycle of the pump.

4. The method according to claim 1, wherein using the pump to advance the air bubble along the tube comprises driving the liquid within the tube that is downstream of the pump to advance along the tube and subsequently exit the tube into a reservoir from which the pump is operatively coupled to pump the liquid.

5. The method according to claim 1, wherein using the pump to continue advancing the air bubble along the tube, past the bubble detector, comprises using the pump to continue advancing the air bubble along the tube, past the pump.

6. The method according to claim 1, wherein using the pump to measure the volume of the air bubble comprises using the bubble detector of the pump to measure the volume of the air bubble.

7. The method according to claim 1, wherein using the pump to measure the volume of the air bubble comprises assessing the number of pumping cycles of the pump during the advancing of the air bubble past the bubble detector of the pump.

8. The method according to claim 1, wherein the method further comprises:
   measuring a value of an air-signal generated by the bubble detector in response to the bubble detector detecting the air bubble; and
   determining if a value of the air-signal is within a predetermined range of values for detection of an air bubble.

9. The method according to claim 8, wherein measuring the value of the air-signal comprises measuring the value of an analog-to-digital (A/D) air signal generated by the bubble detector in response to the bubble detector detecting the air bubble.

10. The method according to claim 1, wherein injecting the air into the tube comprises injecting the air into the tube at a location that is upstream of the pump.

11. The method according to claim 1, wherein occluding the tube downstream of the air bubble comprises occluding the tube downstream of the pump.

12. The method according to claim 1, wherein the pump is a first pump, and wherein the method further comprises, subsequently to step (K):
   (i) removing the occlusion of the tube,
   (ii) disconnecting the first pump from the tube;
   (iii) coupling a second pump to the tube; and
   (iv) repeating steps (B) through (K) using the second pump.

13. The method according to claim 12, wherein repeating steps (B) through (K) using the second pump comprises repeating steps (B) through (K) without repeating step (A) prior to the repeating of steps (B) through (K).

14. The method according to claim 12, wherein repeating steps (B) through (K) comprises using the same tube to repeat steps (B) through (K) 10-50 times using a respective pump each time.

15. The method according to claim 12, wherein the air bubble created in step (B) using the first pump is a first air bubble, and wherein repeating step (B) using the second pump comprises creating a second air bubble in the tube while the first air bubble remains within the tube at a location that is downstream of the pump.

16. The method according to claim 15, wherein repeating steps (B) through (E) using the second pump comprises driving the first air bubble to (i) advance along the tube such that repeating step (F) using the second pump comprises occluding the tube downstream of the second air bubble and not downstream of any part of the first air bubble and subsequently (ii) exit the tube into a reservoir from which the pump is operatively coupled to pump the liquid.

17. The method according to claim 1, wherein using the pump to advance the air bubble along the tube to the bubble detector comprises using the pump to advance the air bubble through a length of tube that is 20-200 cm long.

18. The method according to claim 1, wherein using the pump to advance the air bubble along the tube to the bubble detector comprises using the pump to advance the air bubble from a location that is at a height of 0-100 cm above the pump, with respect to the direction of gravity.

* * * * *